US012605516B2

(12) United States Patent
Tucker et al.

(10) Patent No.: US 12,605,516 B2
(45) Date of Patent: *Apr. 21, 2026

(54) ELECTRONIC CIGARETTE

(71) Applicant: Altria Client Services LLC,
Richmond, VA (US)

(72) Inventors: Christopher S. Tucker, Midlothian, VA
(US); Geoffrey Brandon Jordan,
Midlothian, VA (US); Barry S. Smith,
Richmond, VA (US); Ali A. Rostami,
Richmond, VA (US); Michael J.
Mullins, Richmond, VA (US)

(73) Assignee: Altria Client Services LLC,
Richmond, VA (US)

( * ) Notice: Subject to any disclaimer, the term of this
patent is extended or adjusted under 35
U.S.C. 154(b) by 0 days.

This patent is subject to a terminal dis-
claimer.

(21) Appl. No.: 18/607,997

(22) Filed: Mar. 18, 2024

(65) Prior Publication Data

US 2024/0261521 A1 Aug. 8, 2024

Related U.S. Application Data

(63) Continuation of application No. 17/970,121, filed on
Oct. 20, 2022, now Pat. No. 11,975,143, which is a
(Continued)

(51) Int. Cl.
*A61M 15/06* (2006.01)
*A24F 40/10* (2020.01)
(Continued)

(52) U.S. Cl.
CPC ........... *A61M 15/06* (2013.01); *A24F 40/485*
(2020.01); *A24F 40/70* (2020.01); *A61M*
*11/003* (2014.02);
(Continued)

(58) Field of Classification Search
CPC ......... A24F 40/485; A24F 40/70; H05B 3/10;
H05B 3/16; H05B 3/12
See application file for complete search history.

(56) References Cited

U.S. PATENT DOCUMENTS

| | | |
|---|---|---|
| 539,839 A | 5/1895 | Voron |
| 751,923 A | 2/1904 | Kelly |

(Continued)

FOREIGN PATENT DOCUMENTS

| | | |
|---|---|---|
| AU | 2013214987 B2 | 2/2017 |
| BE | 421623 A | 6/1937 |

(Continued)

OTHER PUBLICATIONS

Notice of Allowance dated Dec. 4, 2024 issued in U.S. Appl. No.
16/784,357.

(Continued)

*Primary Examiner* — Thien S Tran
(74) *Attorney, Agent, or Firm* — Harness, Dickey &
Pierce, P.L.C.

(57) ABSTRACT

An electronic smoking article includes an outer tube extend-
ing in a longitudinal direction, an inner tube within the outer
tube and including a pair of opposing slots, a liquid supply
comprising a liquid material, a coil heater, a wick and a
mouth end insert. The coil heater is located in the inner tube.
The coil heater is formed of an iron-free, nickel-chromium
alloy and has substantially uniformly spaced windings. The
wick is surrounded by the coil heater such that the wick
delivers liquid material to the coil heater and the coil heater
heats the liquid material to a temperature sufficient to
vaporize the liquid material and form an aerosol in the inner
tube.

18 Claims, 5 Drawing Sheets

Related U.S. Application Data continuation of application No. 16/932,003, filed on Jul. 17, 2020, now Pat. No. 11,511,058, which is a continuation of application No. 15/683,135, filed on Aug. 22, 2017, now Pat. No. 10,716,903, which is a continuation of application No. 15/248,116, filed on Aug. 26, 2016, now Pat. No. 9,848,656, which is a continuation of application No. 15/051,001, filed on Feb. 23, 2016, now Pat. No. 9,456,635, which is a continuation of application No. 13/741,254, filed on Jan. 14, 2013, now Pat. No. 9,326,547.

(60) Provisional application No. 61/593,004, filed on Jan. 31, 2012.

(51) Int. Cl.

| | |
|---|---|
| A24F 40/40 | (2020.01) |
| A24F 40/44 | (2020.01) |
| A24F 40/485 | (2020.01) |
| A24F 40/70 | (2020.01) |
| A61M 11/00 | (2006.01) |
| A61M 11/04 | (2006.01) |
| A61M 15/00 | (2006.01) |
| A61M 16/00 | (2006.01) |
| A61M 21/00 | (2006.01) |
| H01C 17/00 | (2006.01) |
| H05B 1/02 | (2006.01) |
| H05B 3/00 | (2006.01) |
| H05B 3/10 | (2006.01) |
| H05B 3/12 | (2006.01) |
| H05B 3/16 | (2006.01) |
| H05B 3/42 | (2006.01) |
| H05B 3/44 | (2006.01) |

(52) U.S. Cl.
CPC .......... *A61M 11/042* (2014.02); *H01C 17/00* (2013.01); *H05B 1/0244* (2013.01); *H05B 3/0014* (2013.01); *H05B 3/10* (2013.01); *H05B 3/12* (2013.01); *H05B 3/16* (2013.01); *H05B 3/42* (2013.01); *H05B 3/44* (2013.01); *A24F 40/10* (2020.01); *A24F 40/40* (2020.01); *A24F 40/44* (2020.01); *A61M 11/001* (2014.02); *A61M 11/04* (2013.01); *A61M 15/002* (2014.02); *A61M 2016/0018* (2013.01); *A61M 2021/0016* (2013.01); *A61M 2205/3653* (2013.01); *A61M 2205/8206* (2013.01); *A61M 2205/8268* (2013.01); *A61M 2209/02* (2013.01); *F04C 2270/0421* (2013.01); *H05B 2203/021* (2013.01); *Y10T 29/49083* (2015.01)

(56) References Cited

U.S. PATENT DOCUMENTS

| | | | |
|---|---|---|---|
| 777,948 | A | 12/1904 | Gable |
| 811,859 | A | 2/1906 | Marsh |
| 962,617 | A | 6/1910 | Bucceri |
| 1,013,157 | A | 1/1912 | Hadaway, Jr. |
| 1,185,661 | A | 6/1916 | Hawley |
| 1,514,682 | A | 11/1924 | Wilson |
| 1,557,351 | A | 10/1925 | Fischer |
| 1,771,366 | A | 7/1930 | Wyss et al. |
| 1,817,546 | A | 8/1931 | Deinstein |
| 1,841,952 | A | 1/1932 | Hughes |
| 1,865,679 | A | 7/1932 | Colpe |
| 1,865,780 | A | 7/1932 | Naimaster |
| 1,916,799 | A | 7/1933 | Hughes |
| 1,968,509 | A | 7/1934 | Tiffany |
| 2,057,353 | A | 10/1936 | Whittlemore, Jr. |
| 2,104,266 | A | 1/1938 | McCormick |
| 2,356,975 | A | 8/1944 | Comptois |
| 2,406,275 | A | 8/1946 | Wejnarth |
| 2,442,004 | A | 5/1948 | Hayward-Butt |
| 2,542,612 | A | 2/1951 | Arneson |
| 2,558,127 | A | 6/1951 | Downs |
| 2,599,310 | A | 6/1952 | Alexander |
| 2,609,817 | A | 9/1952 | Falcone |
| 2,670,739 | A | 3/1954 | Mcneill |
| 2,746,890 | A | 5/1956 | Legler |
| 2,836,183 | A | 5/1958 | Fay et al. |
| 2,907,686 | A | 10/1959 | Siegel |
| 2,971,039 | A | 2/1961 | Western |
| 2,972,557 | A | 2/1961 | Toulmin, Jr. |
| 2,974,669 | A | 3/1961 | Ellis |
| 3,062,218 | A | 11/1962 | Temkovits |
| 3,150,668 | A | 9/1964 | Lassiter et al. |
| 3,160,946 | A | 12/1964 | Dickson, Jr. |
| 3,200,819 | A | 8/1965 | Gilbert |
| 3,255,760 | A | 6/1966 | Selker |
| 3,258,015 | A | 6/1966 | Ellis et al. |
| 3,294,095 | A | 12/1966 | Ackerman |
| 3,347,231 | A | 10/1967 | Chang |
| 3,356,094 | A | 12/1967 | Ellis et al. |
| 3,363,633 | A | 1/1968 | Weber |
| 3,396,733 | A | 8/1968 | Allseits et al. |
| 3,402,723 | A | 9/1968 | Hu |
| 3,425,414 | A | 2/1969 | La |
| 3,428,050 | A | 2/1969 | Kandel |
| 3,439,685 | A | 4/1969 | Allen |
| 3,482,580 | A | 12/1969 | Hollabaugh |
| 3,521,643 | A | 7/1970 | Toth |
| 3,559,300 | A | 2/1971 | Fox |
| 3,581,748 | A | 6/1971 | Cameron |
| 3,587,573 | A | 6/1971 | Flack |
| 3,608,560 | A | 9/1971 | Briskin et al. |
| 3,631,856 | A | 1/1972 | Taylor |
| 3,681,018 | A | 8/1972 | Karl-Georg et al. |
| 3,685,527 | A | 8/1972 | Sherrill |
| 3,721,240 | A | 3/1973 | Tamburri |
| 3,738,374 | A | 6/1973 | Bennett |
| 3,744,496 | A | 7/1973 | McCarty et al. |
| D229,789 | S | 1/1974 | Berger |
| 3,789,840 | A | 2/1974 | Rosenblatt |
| 3,804,100 | A | 4/1974 | Fariello |
| 3,828,799 | A | 8/1974 | Beam |
| 3,875,476 | A | 4/1975 | Crandall et al. |
| 3,878,041 | A | 4/1975 | Leitnaker et al. |
| 3,886,954 | A | 6/1975 | Hannema et al. |
| 3,889,690 | A | 6/1975 | Guarnieri |
| 3,895,219 | A | 7/1975 | Richerson et al. |
| 3,943,941 | A | 3/1976 | Boyd et al. |
| 4,016,061 | A | 4/1977 | Wasa et al. |
| 4,068,672 | A | 1/1978 | Guerra |
| 4,077,784 | A | 3/1978 | Vayrynen |
| 4,083,372 | A | 4/1978 | Boden |
| 4,098,725 | A | 7/1978 | Yamamoto et al. |
| 4,110,260 | A | 8/1978 | Yamamoto et al. |
| 4,131,119 | A | 12/1978 | Blasutti |
| 4,141,369 | A | 2/1979 | Burruss |
| 4,149,548 | A | 4/1979 | Bradshaw |
| 4,164,230 | A | 8/1979 | Pearlman |
| 4,193,411 | A | 3/1980 | Faris et al. |
| 4,215,708 | A | 8/1980 | Bron |
| 4,219,032 | A | 8/1980 | Tabatznik et al. |
| 4,246,913 | A | 1/1981 | Ogden et al. |
| 4,256,945 | A | 3/1981 | Carter et al. |
| 4,259,970 | A | 4/1981 | Green, Jr. |
| 4,275,747 | A | 6/1981 | Miller |
| 4,284,089 | A | 8/1981 | Ray |
| 4,331,166 | A | 5/1982 | Hale |
| 4,413,641 | A | 11/1983 | Dwyer, Jr. et al. |
| 4,419,302 | A | 12/1983 | Nishino et al. |
| 4,429,703 | A | 2/1984 | Haber |
| 4,430,072 | A | 2/1984 | Kellogg et al. |
| 4,446,878 | A | 5/1984 | Porenski, Jr. |
| 4,457,319 | A | 7/1984 | Lamb et al. |
| 4,476,882 | A | 10/1984 | Luke |
| 4,493,331 | A | 1/1985 | Porenski, Jr. |
| 4,506,683 | A | 3/1985 | Cantrell et al. |

(56)                  References Cited

U.S. PATENT DOCUMENTS

| | | | |
|---|---|---|---|
| 4,515,170 A | 5/1985 | Cantrell et al. |
| 4,517,996 A | 5/1985 | Vester |
| 4,582,072 A | 4/1986 | Sanford |
| 4,620,557 A | 11/1986 | Cantrell et al. |
| 4,649,944 A | 3/1987 | Houck, Jr. et al. |
| 4,649,945 A | 3/1987 | Norman et al. |
| 4,681,125 A | 7/1987 | Johnson |
| 4,687,008 A | 8/1987 | Houck, Jr. et al. |
| 4,700,725 A * | 10/1987 | Geiszler, Jr. .......... A24D 3/041 |
| | | 131/338 |
| 4,735,217 A | 4/1988 | Gerth et al. |
| 4,765,347 A | 8/1988 | Sensabaugh, Jr. et al. |
| 4,776,353 A | 10/1988 | Lilja et al. |
| 4,804,002 A | 2/1989 | Herron |
| 4,848,376 A | 7/1989 | Lilja et al. |
| 4,922,901 A | 5/1990 | Brooks et al. |
| 4,941,486 A | 7/1990 | Dube et al. |
| 4,945,929 A | 8/1990 | Egilmex |
| 4,945,931 A | 8/1990 | Gori |
| 4,947,874 A | 8/1990 | Brooks et al. |
| 4,947,875 A | 8/1990 | Brooks et al. |
| 4,966,171 A | 10/1990 | Serrano et al. |
| 4,981,522 A | 1/1991 | Nichols et al. |
| 4,991,606 A | 2/1991 | Serrano et al. |
| 4,993,436 A | 2/1991 | Bloom, Jr. |
| 5,000,228 A | 3/1991 | Manent et al. |
| 5,016,656 A | 5/1991 | McMurtrie |
| 5,040,552 A | 8/1991 | Schleich et al. |
| 5,042,510 A | 8/1991 | Curtiss et al. |
| 5,045,237 A | 9/1991 | Washburn |
| 5,060,671 A | 10/1991 | Counts et al. |
| 5,076,296 A | 12/1991 | Nystrom et al. |
| 5,085,804 A | 2/1992 | Washburn |
| 5,093,894 A | 3/1992 | Deevi et al. |
| 5,095,921 A | 3/1992 | Losee et al. |
| 5,116,298 A | 5/1992 | Bondanelli et al. |
| 5,137,578 A | 8/1992 | Chan |
| 5,139,594 A | 8/1992 | Rabin |
| 5,144,962 A | 9/1992 | Counts et al. |
| 5,144,964 A | 9/1992 | Demain |
| 5,157,242 A | 10/1992 | Hetherington et al. |
| 5,159,940 A | 11/1992 | Hayward et al. |
| 5,179,966 A | 1/1993 | Losee et al. |
| 5,224,498 A | 7/1993 | Deevi et al. |
| 5,228,460 A | 7/1993 | Sprinkel et al. |
| 5,235,157 A | 8/1993 | Blackburn |
| 5,249,586 A | 10/1993 | Morgan et al. |
| 5,269,327 A | 12/1993 | Counts et al. |
| 5,274,214 A | 12/1993 | Blackburn |
| 5,285,050 A | 2/1994 | Blackburn |
| 5,322,075 A | 6/1994 | Deevi et al. |
| 5,353,813 A | 10/1994 | Deevi et al. |
| 5,369,723 A | 11/1994 | Counts et al. |
| 5,388,594 A | 2/1995 | Counts et al. |
| 5,396,911 A | 3/1995 | Casey, III et al. |
| 5,408,574 A | 4/1995 | Deevi et al. |
| 5,473,251 A | 12/1995 | Mori |
| 5,498,855 A | 3/1996 | Deevi et al. |
| 5,505,214 A | 4/1996 | Collins et al. |
| 5,514,630 A | 5/1996 | Willkens et al. |
| 5,591,368 A | 1/1997 | Fleischhauer et al. |
| 5,595,706 A | 1/1997 | Sikka et al. |
| 5,611,360 A | 3/1997 | Tang |
| 5,613,504 A | 3/1997 | Collins et al. |
| 5,613,505 A | 3/1997 | Campbell et al. |
| 5,665,262 A | 9/1997 | Hajaligol et al. |
| 5,666,977 A | 9/1997 | Higgins et al. |
| 5,666,978 A | 9/1997 | Counts et al. |
| 5,692,291 A | 12/1997 | Deevi et al. |
| 5,724,997 A | 3/1998 | Smith et al. |
| 5,730,158 A | 3/1998 | Collins et al. |
| 5,743,251 A | 4/1998 | Howell et al. |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,924,417 A | 7/1999 | Braithwaite |
| 5,935,975 A | 8/1999 | Rose et al. |
| 6,006,757 A | 12/1999 | Lichtenberg |
| 6,016,801 A | 1/2000 | Philips |
| 6,026,820 A | 2/2000 | Baggett, Jr. et al. |
| 6,089,857 A * | 7/2000 | Matsuura .............. A61M 15/06 |
| | | 431/153 |
| 6,155,268 A | 12/2000 | Takeuchi |
| 6,164,287 A | 12/2000 | White |
| 6,196,218 B1 | 3/2001 | Voges |
| 6,234,167 B1 | 5/2001 | Cox et al. |
| 6,371,127 B1 | 4/2002 | Snaidr et al. |
| 6,443,146 B1 | 9/2002 | Voges |
| 6,516,796 B1 | 2/2003 | Cox et al. |
| 6,598,607 B2 | 7/2003 | Adiga et al. |
| 6,615,840 B1 | 9/2003 | Fournier et al. |
| 6,715,487 B2 | 4/2004 | Nichols et al. |
| 6,772,756 B2 | 8/2004 | Shayan |
| 6,806,682 B2 | 10/2004 | Hsiao |
| 6,810,883 B2 | 11/2004 | Felter et al. |
| 6,854,470 B1 | 2/2005 | Pu |
| 6,994,096 B2 | 2/2006 | Rostami et al. |
| 7,073,499 B1 | 7/2006 | Reinhold et al. |
| 7,117,867 B2 | 10/2006 | Cox et al. |
| 7,131,599 B2 | 11/2006 | Katase |
| 7,167,641 B2 | 1/2007 | Tam et al. |
| 7,381,277 B2 | 6/2008 | Gonterman et al. |
| 7,404,405 B1 | 7/2008 | Mehio |
| 7,458,374 B2 | 12/2008 | Hale et al. |
| D590,988 S | 4/2009 | Hon |
| D590,989 S | 4/2009 | Hon |
| D590,990 S | 4/2009 | Hon |
| D590,991 S | 4/2009 | Hon |
| 7,527,059 B2 | 5/2009 | Iannuzzi |
| 7,614,402 B2 | 11/2009 | Gomes |
| 7,726,320 B2 | 6/2010 | Robinson et al. |
| 7,789,089 B2 | 9/2010 | Dube et al. |
| 7,810,508 B2 | 10/2010 | Wyss-Peters et al. |
| 7,832,410 B2 | 11/2010 | Hon |
| 7,845,359 B2 | 12/2010 | Montaser |
| 7,878,962 B2 | 2/2011 | Karles et al. |
| 7,906,936 B2 | 3/2011 | Azancot et al. |
| 7,913,688 B2 | 3/2011 | Cross et al. |
| 7,920,777 B2 | 4/2011 | Rabin et al. |
| 7,938,124 B2 | 5/2011 | Izumiya et al. |
| 7,952,322 B2 | 5/2011 | Partovi et al. |
| 7,997,280 B2 | 8/2011 | Rosenthal |
| D646,431 S | 10/2011 | Awty et al. |
| D651,338 S | 12/2011 | Awty et al. |
| 8,079,371 B2 | 12/2011 | Robinson et al. |
| D653,390 S | 1/2012 | Kaljura |
| D655,036 S | 2/2012 | Zhou |
| 8,113,215 B2 | 2/2012 | Rasouli et al. |
| 8,118,161 B2 | 2/2012 | Guerrera et al. |
| 8,127,772 B2 | 3/2012 | Montaser |
| 8,156,944 B2 | 4/2012 | Han |
| 8,157,918 B2 | 4/2012 | Becker et al. |
| 8,196,576 B2 | 6/2012 | Kriksunov et al. |
| 8,205,622 B2 | 6/2012 | Pan |
| 8,258,192 B2 | 9/2012 | Wu et al. |
| 8,314,591 B2 | 11/2012 | Terry et al. |
| 8,365,742 B2 | 2/2013 | Hon |
| 8,371,310 B2 | 2/2013 | Brenneise |
| 8,375,957 B2 | 2/2013 | Hon |
| 8,393,331 B2 | 3/2013 | Hon |
| D684,311 S | 6/2013 | Liu |
| 8,459,270 B2 | 6/2013 | Coven et al. |
| 8,459,271 B2 | 6/2013 | Inagaki |
| 8,499,766 B1 | 8/2013 | Newton |
| 8,511,318 B2 | 8/2013 | Hon |
| 8,550,068 B2 | 10/2013 | Terry et al. |
| 8,550,069 B2 | 10/2013 | Alelov |
| 8,689,805 B2 | 4/2014 | Hon |
| 8,833,364 B2 | 9/2014 | Buchberger |
| 8,915,254 B2 | 12/2014 | Monsees et al. |
| 8,960,197 B2 | 2/2015 | Bailey et al. |
| 9,078,473 B2 | 7/2015 | Worm et al. |
| 9,078,474 B2 | 7/2015 | Thompson |

(56) References Cited

U.S. PATENT DOCUMENTS

| | | |
|---|---|---|
| 9,204,670 B2 | 12/2015 | Liu |
| 9,282,772 B2 | 3/2016 | Tucker et al. |
| 9,326,547 B2 | 5/2016 | Tucker et al. |
| 9,351,522 B2 | 5/2016 | Safari |
| 9,408,416 B2 | 8/2016 | Monsees et al. |
| 9,474,306 B2 | 10/2016 | Tucker et al. |
| 9,510,623 B2 | 12/2016 | Tucker et al. |
| 9,854,839 B2 | 1/2018 | Tucker et al. |
| 2002/0005207 A1 | 1/2002 | Wrenn et al. |
| 2002/0179101 A1 | 12/2002 | Chavez |
| 2004/0020500 A1 | 2/2004 | Wrenn et al. |
| 2004/0050396 A1 | 3/2004 | Squeo |
| 2004/0099266 A1 | 5/2004 | Cross et al. |
| 2004/0149296 A1 | 8/2004 | Rostami et al. |
| 2005/0016550 A1 | 1/2005 | Katase |
| 2005/0016553 A1 | 1/2005 | Iannuzzi |
| 2005/0067503 A1 | 3/2005 | Katase |
| 2005/0126651 A1 | 6/2005 | Sherwin |
| 2005/0175331 A1 | 8/2005 | Tam et al. |
| 2005/0279371 A1 | 12/2005 | Billard et al. |
| 2006/0070633 A1 | 4/2006 | Rostami et al. |
| 2006/0191546 A1 | 8/2006 | Takano et al. |
| 2006/0196518 A1 | 9/2006 | Hon |
| 2006/0254604 A1 | 11/2006 | Martinez Fernandez |
| 2007/0074734 A1 | 4/2007 | Braunshteyn et al. |
| 2007/0095357 A1 | 5/2007 | Besso et al. |
| 2007/0098148 A1* | 5/2007 | Sherman ................. H04M 1/21 |
| | | 379/451 |
| 2007/0102013 A1 | 5/2007 | Adams et al. |
| 2007/0267031 A1 | 11/2007 | Hon |
| 2007/0267032 A1 | 11/2007 | Shan |
| 2007/0279002 A1 | 12/2007 | Partovi |
| 2007/0280653 A1 | 12/2007 | Viera |
| 2007/0295332 A1 | 12/2007 | Ziegler et al. |
| 2008/0038363 A1 | 2/2008 | Zaffaroni et al. |
| 2008/0047571 A1 | 2/2008 | Braunshteyn et al. |
| 2008/0053465 A1 | 3/2008 | Tarora et al. |
| 2008/0092912 A1* | 4/2008 | Robinson ................. H05B 3/42 |
| | | 131/200 |
| 2008/0230052 A1 | 9/2008 | Montaser |
| 2008/0276947 A1 | 11/2008 | Martzel |
| 2009/0007925 A1 | 1/2009 | Rasouli et al. |
| 2009/0012655 A1 | 1/2009 | Kienman et al. |
| 2009/0044816 A1 | 2/2009 | Rasouli et al. |
| 2009/0056729 A1 | 3/2009 | Zawadzki et al. |
| 2009/0065011 A1 | 3/2009 | Maeder et al. |
| 2009/0084391 A1 | 4/2009 | Krupp |
| 2009/0095311 A1 | 4/2009 | Han |
| 2009/0126745 A1 | 5/2009 | Hon |
| 2009/0133704 A1 | 5/2009 | Strickland et al. |
| 2009/0139517 A1* | 6/2009 | Wachtel ............ A61M 15/0061 |
| | | 222/394 |
| 2009/0139533 A1 | 6/2009 | Park et al. |
| 2009/0151717 A1 | 6/2009 | Bowen et al. |
| 2009/0162294 A1 | 6/2009 | Werner |
| 2009/0188490 A1 | 7/2009 | Han |
| 2009/0230117 A1 | 9/2009 | Fernando et al. |
| 2009/0272379 A1* | 11/2009 | Thorens ................. A61M 15/06 |
| | | 219/535 |
| 2009/0283103 A1 | 11/2009 | Nielsen et al. |
| 2009/0293892 A1 | 12/2009 | Williams et al. |
| 2009/0301502 A1 | 12/2009 | Mehio |
| 2010/0031968 A1 | 2/2010 | Sheikh et al. |
| 2010/0083959 A1 | 4/2010 | Siller |
| 2010/0126505 A1 | 5/2010 | Rinker |
| 2010/0200006 A1 | 8/2010 | Robinson et al. |
| 2010/0200008 A1 | 8/2010 | Taieb |
| 2010/0206317 A1 | 8/2010 | Albino et al. |
| 2010/0242974 A1 | 9/2010 | Pan |
| 2010/0242975 A1 | 9/2010 | Hearn |
| 2010/0242976 A1 | 9/2010 | Katayama et al. |
| 2010/0275938 A1 | 11/2010 | Roth et al. |
| 2010/0307518 A1 | 12/2010 | Wang |
| 2011/0005535 A1 | 1/2011 | Xiu |
| 2011/0011394 A1 | 1/2011 | Edwards et al. |
| 2011/0011396 A1 | 1/2011 | Fang |
| 2011/0036346 A1 | 2/2011 | Cohen et al. |
| 2011/0036363 A1 | 2/2011 | Urtsev et al. |
| 2011/0036367 A1 | 2/2011 | Saito et al. |
| 2011/0088707 A1 | 4/2011 | Hajaligol |
| 2011/0094523 A1 | 4/2011 | Thorens et al. |
| 2011/0120455 A1 | 5/2011 | Murphy |
| 2011/0120482 A1 | 5/2011 | Brenneise |
| 2011/0126848 A1 | 6/2011 | Zuber et al. |
| 2011/0147486 A1 | 6/2011 | Greim et al. |
| 2011/0155153 A1 | 6/2011 | Thorens et al. |
| 2011/0168194 A1 | 7/2011 | Hon |
| 2011/0209717 A1 | 9/2011 | Han |
| 2011/0220134 A1 | 9/2011 | Duke et al. |
| 2011/0226236 A1 | 9/2011 | Buchberger |
| 2011/0232654 A1 | 9/2011 | Mass |
| 2011/0245493 A1 | 10/2011 | Rabinowitz et al. |
| 2011/0253798 A1 | 10/2011 | Tucker et al. |
| 2011/0265806 A1 | 11/2011 | Alarcon et al. |
| 2011/0277756 A1 | 11/2011 | Terry et al. |
| 2011/0277757 A1 | 11/2011 | Terry et al. |
| 2011/0277760 A1 | 11/2011 | Terry et al. |
| 2011/0277761 A1 | 11/2011 | Terry et al. |
| 2011/0277764 A1 | 11/2011 | Terry et al. |
| 2011/0277780 A1 | 11/2011 | Terry et al. |
| 2011/0278189 A1 | 11/2011 | Terry et al. |
| 2011/0290244 A1 | 12/2011 | Schennum |
| 2011/0290268 A1 | 12/2011 | Schennum |
| 2011/0303231 A1* | 12/2011 | Li ........................... A24F 40/42 |
| | | 131/329 |
| 2011/0304282 A1 | 12/2011 | Li et al. |
| 2012/0006342 A1 | 1/2012 | Rose et al. |
| 2012/0048266 A1 | 3/2012 | Alelov |
| 2012/0090629 A1 | 4/2012 | Turner et al. |
| 2012/0111347 A1 | 5/2012 | Hon |
| 2012/0118301 A1 | 5/2012 | Montaser |
| 2012/0145169 A1 | 6/2012 | Wu |
| 2012/0167906 A1 | 7/2012 | Gysland |
| 2012/0174914 A1 | 7/2012 | Pirshafiey et al. |
| 2012/0186594 A1 | 7/2012 | Liu |
| 2012/0199146 A1 | 8/2012 | Marangos |
| 2012/0199663 A1 | 8/2012 | Qiu |
| 2012/0201522 A1 | 8/2012 | Stauffer et al. |
| 2012/0211015 A1 | 8/2012 | Li et al. |
| 2012/0227753 A1 | 9/2012 | Newton |
| 2012/0230659 A1 | 9/2012 | Goodman et al. |
| 2012/0260927 A1 | 10/2012 | Liu |
| 2012/0285475 A1 | 11/2012 | Liu |
| 2012/0285476 A1 | 11/2012 | Hon |
| 2012/0312313 A1 | 12/2012 | Frija |
| 2012/0318882 A1 | 12/2012 | Abehasera |
| 2012/0325227 A1 | 12/2012 | Robinson et al. |
| 2013/0014772 A1 | 1/2013 | Liu |
| 2013/0019887 A1 | 1/2013 | Liu |
| 2013/0025609 A1 | 1/2013 | Liu |
| 2013/0026798 A1 | 1/2013 | Meier |
| 2013/0032159 A1 | 2/2013 | Capuano |
| 2013/0032161 A1 | 2/2013 | Herholdt |
| 2013/0037041 A1 | 2/2013 | Worm et al. |
| 2013/0061861 A1 | 3/2013 | Hearn |
| 2013/0081642 A1 | 4/2013 | Safari |
| 2013/0087160 A1 | 4/2013 | Gherghe |
| 2013/0118509 A1 | 5/2013 | Richardson |
| 2013/0125906 A1 | 5/2013 | Hon |
| 2013/0139833 A1 | 6/2013 | Hon |
| 2013/0152922 A1 | 6/2013 | Benassayag et al. |
| 2013/0168880 A1 | 7/2013 | Duke |
| 2013/0192615 A1 | 8/2013 | Tucker et al. |
| 2013/0192616 A1 | 8/2013 | Tucker et al. |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2013/0206154 A1 | 8/2013 | Fernando et al. |
| 2013/0213418 A1 | 8/2013 | Tucker et al. |
| 2013/0213419 A1 | 8/2013 | Tucker et al. |
| 2013/0213420 A1 | 8/2013 | Hon |
| 2013/0220315 A1 | 8/2013 | Conley et al. |

(56) References Cited

U.S. PATENT DOCUMENTS

| | | | |
|---|---|---|---|
| 2013/0228191 A1* | 9/2013 | Newton | A61M 15/06 |
| | | | 131/329 |
| 2013/0263869 A1 | 10/2013 | Zhu | |
| 2013/0276798 A1 | 10/2013 | Hon | |
| 2013/0298905 A1 | 11/2013 | Levin et al. | |
| 2013/0300350 A1 | 11/2013 | Xiang | |
| 2013/0319440 A1 | 12/2013 | Capuano | |
| 2014/0000638 A1 | 1/2014 | Sebastian et al. | |
| 2014/0007863 A1 | 1/2014 | Chen | |
| 2014/0034071 A1 | 2/2014 | Levitz et al. | |
| 2014/0196718 A1 | 7/2014 | Li et al. | |
| 2014/0209110 A1 | 7/2014 | Hon | |
| 2014/0262869 A1 | 9/2014 | Fath et al. | |
| 2014/0262871 A1 | 9/2014 | Fath | |
| 2014/0262931 A1 | 9/2014 | Fath | |
| 2014/0338680 A1 | 11/2014 | Abramov et al. | |
| 2015/0020831 A1 | 1/2015 | Weigensberg et al. | |
| 2015/0128974 A1 | 5/2015 | Hon | |
| 2015/0250232 A1 | 9/2015 | Hon | |

FOREIGN PATENT DOCUMENTS

| | | | |
|---|---|---|---|
| CA | 1202378 A | 3/1986 | |
| CH | 421786 A | 9/1966 | |
| CH | 698603 B1 | 9/2009 | |
| CN | 87/104459 A | 2/1988 | |
| CN | 2243191 Y | 12/1996 | |
| CN | 1191696 A | 9/1998 | |
| CN | 1196660 A | 10/1998 | |
| CN | 2293953 Y | 10/1998 | |
| CN | 1229616 A | 9/1999 | |
| CN | 2719043 Y | 8/2005 | |
| CN | 277799 | 5/2006 | |
| CN | 2777995 Y | 5/2006 | |
| CN | 1906096 A | 1/2007 | |
| CN | 2889333 Y | 4/2007 | |
| CN | 101116542 A | 2/2008 | |
| CN | 201018927 Y | 2/2008 | |
| CN | 201029436 Y | 3/2008 | |
| CN | 100377672 C | 4/2008 | |
| CN | 201054977 Y | 5/2008 | |
| CN | 201067079 Y | 6/2008 | |
| CN | 201076006 Y | 6/2008 | |
| CN | 201079011 Y | 7/2008 | |
| CN | 201085044 Y | 7/2008 | |
| CN | 201108031 Y | 9/2008 | |
| CN | 201127293 Y | 10/2008 | |
| CN | 201146824 Y | 11/2008 | |
| CN | 10132257 | 12/2008 | |
| CN | 101322579 A | 12/2008 | |
| CN | 201238610 Y | 5/2009 | |
| CN | 101518361 A | 9/2009 | |
| CN | 101524187 A | 9/2009 | |
| CN | 101557728 A | 10/2009 | |
| CN | 201379072 Y | 1/2010 | |
| CN | 101843368 A | 9/2010 | |
| CN | 20170939 | 1/2011 | |
| CN | 201709398 U | 1/2011 | |
| CN | 101983018 A | 3/2011 | |
| CN | 201767027 U | 3/2011 | |
| CN | 20178992 | 4/2011 | |
| CN | 20179799 | 4/2011 | |
| CN | 101606758 B | 4/2011 | |
| CN | 102014996 A | 4/2011 | |
| CN | 201789924 U | 4/2011 | |
| CN | 201797997 U | 4/2011 | |
| CN | 201830900 U | 5/2011 | |
| CN | 10210661 | 6/2011 | |
| CN | 102106611 A | 6/2011 | |
| CN | 201860753 U | 6/2011 | |
| CN | 201869778 U | 6/2011 | |
| CN | 10216604 | 8/2011 | |
| CN | 102166044 A | 8/2011 | |
| CN | 201986689 U | 9/2011 | |
| CN | 202014571 | 10/2011 | |
| CN | 202014571 U | 10/2011 | |
| CN | 202014572 U | 10/2011 | |
| CN | 202026802 | 10/2011 | |
| CN | 102264420 A | 11/2011 | |
| CN | 102264423 A | 11/2011 | |
| CN | 202026804 U | 11/2011 | |
| CN | 102266125 A | 12/2011 | |
| CN | 202068930 U | 12/2011 | |
| CN | 202068932 U | 12/2011 | |
| CN | 202122097 U | 1/2012 | |
| CN | 202145881 U | 2/2012 | |
| CN | 202179125 U | 4/2012 | |
| CN | 202233005 U | 5/2012 | |
| CN | 202233007 U | 5/2012 | |
| CN | 202262413 U | 6/2012 | |
| CN | 202286307 U | 7/2012 | |
| CN | 102655773 A | 9/2012 | |
| CN | 202445135 U | 9/2012 | |
| CN | 102740716 A | 10/2012 | |
| CN | 202456410 U | 10/2012 | |
| CN | 202525085 U | 11/2012 | |
| CN | 202603603 U | 12/2012 | |
| CN | 202603608 U | 12/2012 | |
| CN | 102894485 A | 1/2013 | |
| DE | 3640917 A1 | 8/1988 | |
| DE | 3735704 A1 | 5/1989 | |
| DE | 19854009 A1 | 5/2000 | |
| DE | 19935706 A1 | 2/2001 | |
| DE | 69824982 T2 | 10/2004 | |
| DE | 202010011436 U1 | 11/2010 | |
| EP | 0893071 A1 | 7/1908 | |
| EP | 0117355 A2 | 9/1984 | |
| EP | 0277519 A2 | 8/1988 | |
| EP | 0295122 A2 | 12/1988 | |
| EP | 0358002 A2 | 3/1990 | |
| EP | 0358114 A2 | 3/1990 | |
| EP | 0430566 A2 | 6/1991 | |
| EP | 438862 A2 | 7/1991 | |
| EP | 0488488 A1 | 6/1992 | |
| EP | 0503767 A1 | 9/1992 | |
| EP | 0608783 A1 | 8/1994 | |
| EP | 0845220 A1 | 6/1998 | |
| EP | 0857431 A1 | 8/1998 | |
| EP | 1618803 A1 | 1/2006 | |
| EP | 1736065 A1 | 12/2006 | |
| EP | 1989946 A1 | 11/2008 | |
| EP | 2022350 A1 | 2/2009 | |
| EP | 2110033 A1 | 10/2009 | |
| EP | 2113178 A1 | 11/2009 | |
| EP | 2260733 A1 | 12/2010 | |
| EP | 2481308 A1 | 8/2012 | |
| EP | 2809180 B1 | 12/2019 | |
| ES | 1070376 Y | 11/2009 | |
| GB | 203964 | 9/1923 | |
| GB | 2148079 A | 5/1985 | |
| GB | 2406780 A | 4/2005 | |
| JP | 61068061 A | 4/1986 | |
| JP | H11164679 A | 6/1999 | |
| JP | 2003527127 A | 9/2003 | |
| JP | 2006/320286 A | 11/2006 | |
| JP | 2007511437 A | 5/2007 | |
| JP | 2009-537120 A | 10/2009 | |
| JP | 2010-104310 A | 5/2010 | |
| JP | 2010-213579 A | 9/2010 | |
| JP | 3164992 U | 12/2010 | |
| KR | 100636287 B1 | 10/2006 | |
| KR | 200454110 Y1 | 6/2011 | |
| KR | 2011-0006928 U | 7/2011 | |
| KR | 101081481 B1 | 11/2011 | |
| KR | 20110010862 U | 11/2011 | |
| KR | 200457340 Y1 | 12/2011 | |
| NL | 8201585 A | 11/1982 | |
| RU | 94815 U1 | 6/2010 | |
| WO | WO-86/02528 A1 | 5/1986 | |
| WO | WO-9003224 A1 | 4/1990 | |
| WO | WO-95/02970 A1 | 2/1995 | |
| WO | WO-97/048293 A1 | 12/1997 | |
| WO | WO-9843019 A1 | 10/1998 | |

(56) References Cited

FOREIGN PATENT DOCUMENTS

| WO | WO-00/28843 A1 | 5/2000 |
| WO | WO-0170054 A1 | 9/2001 |
| WO | WO-03037412 A2 | 5/2003 |
| WO | WO-03/080149 A2 | 10/2003 |
| WO | WO-2004/043175 A1 | 5/2004 |
| WO | WO-2004/054647 A1 | 7/2004 |
| WO | WO-2004/080216 A1 | 9/2004 |
| WO | WO-2004/095955 A1 | 11/2004 |
| WO | WO-2005049449 A1 | 6/2005 |
| WO | WO-2005/099494 A1 | 10/2005 |
| WO | WO-2005120614 A1 | 12/2005 |
| WO | WO-2007024130 A1 | 3/2007 |
| WO | WO-2007/066374 A1 | 6/2007 |
| WO | WO-2007/078273 A1 | 7/2007 |
| WO | WO-2007/098337 A2 | 8/2007 |
| WO | WO-2007/131449 A1 | 11/2007 |
| WO | WO-2007/131450 A1 | 11/2007 |
| WO | WO-2007/141668 A2 | 12/2007 |
| WO | WO-2008/055423 A1 | 5/2008 |
| WO | WO-2009135729 A1 | 11/2009 |
| WO | WO-2010091593 A1 | 8/2010 |
| WO | WO-2010/145468 A1 | 12/2010 |
| WO | WO-2011015825 A1 | 2/2011 |
| WO | WO-2011/050943 A1 | 5/2011 |
| WO | WO-2011/121326 A2 | 10/2011 |
| WO | WO-2011/124033 A1 | 10/2011 |
| WO | WO-2011/125058 A1 | 10/2011 |
| WO | WO-2011/146372 A2 | 11/2011 |
| WO | WO-2011146174 A2 | 11/2011 |
| WO | WO-2011147714 A1 | 12/2011 |
| WO | WO-2012/088675 A1 | 7/2012 |
| WO | WO-2012/109371 A2 | 8/2012 |
| WO | WO-2012117578 A1 * | 9/2012 | ............. A24F 13/00 |
| WO | WO-2012/129787 A1 | 10/2012 |
| WO | WO-2012/129812 A1 | 10/2012 |
| WO | WO-2012/142293 A2 | 10/2012 |
| WO | WO-2012/152053 A1 | 11/2012 |
| WO | WO-2013116565 A1 | 8/2013 |

OTHER PUBLICATIONS

Notice of Allowance dated Jan. 15, 2025 issued in U.S. Appl. No. 17/970,135.
Decision dated Nov. 14, 2024 issued in European patent No. 2809184.
Extended European Search Report dated Mar. 20, 2024 issued in European patent application No. 24159503.2.
Office Action dated May 28, 2024 issued in U.S. Appl. No. 16/784,357.
International Search Report and Written Opinion for PCT/US13/24228 dated Apr. 9, 2013.
International Search Report and Written Opinion for PCT/US13/24229 dated Apr. 22, 2013.
International Search Report and Written Opinion for PCT/US13/24215 dated Apr. 22, 2013.
International Search Report and Written Opinion for PCT/US13/24222 dated Apr. 24, 2013.
International Search Report and Written Opinion for PCT/US13/27424 dated Apr. 25, 2013.
International Search Report and Written Opinion for PCT/US13/24224 dated May 13, 2013.
U.S. Appl. No. 13/843,028, filed Mar. 15, 2013, to Fath et al.
U.S. Appl. No. 13/843,449, filed Mar. 15, 2013, to Fath et al.
International Search Report and Written Opinion for PCT/US13/24219 dated Apr. 22, 2013.
U.S. Appl. No. 13/843,314, filed Mar. 15, 2013, to Fath et al.
International Search Report and Written Opinion for PCT/US13/24211 dated Apr. 19, 2013.
DE 19935706 Translation; Feb. 2001, Kumar Zubide.
Moroccan Office Action dated Mar. 13, 2015 issued in corresponding Moroccan Application No. 37287.

European Search Report dated May 29, 2015 issued in corresponding European Patent Application No. 13744358.6.
European Search Report dated Jul. 9, 2015 issued in corresponding European Patent Application No. 13743475.9.
Office Action for corresponding Chinese application No. 201380007594.2 dated Nov. 23, 2015 and English Translation thereof.
Notice of Allowance for co-related U.S. Appl. No. 13/741,217 dated Nov. 9, 2015.
Office Action for corresponding Chinese application No. 201380018495.4 dated Jan. 4, 2016 and English Translation thereof.
Kazakhstan Office Action dated Mar. 11, 2016 for corresponding KZ Application No. 2014/1685.1.
USPTO non-final Office Action dated Apr. 5, 2016 in U.S. Appl. No. 13/756,127.
International Search Report and Written Opinion for PCT/US13/27432 dated May 2, 2013.
International Preliminary Report on Patentability for PCT/US2013/024215 dated Aug. 14, 2014.
Russian Office Action dated Jul. 14, 2016 for corresponding Application No. 2014135386.
Office Action for corresponding Russian application No. 2014135380 dated Aug. 8, 2016 and English translation thereof.
U.S. Office Action U.S. Appl. No. 15/049,573 dated Aug. 26, 2016.
Office Action for corresponding Chinese application No. 201380018578.3 dated Aug. 23, 2016 and English translation thereof.
International Search Report and Written Opinion for PCT/US13/27432 dated May 2, 2013.
International Preliminary Report on Patentability for PCT/US2013/024229 dated Aug. 14, 2014.
European Search Report dated May 29, 2015 issued in corresponding European Application No. 13744145.7.
Office Action for corresponding Chinese application No. 201380018578.3 dated Dec. 25, 2015 and English Translation thereof.
New Zealand Office Action dated Jun. 20, 2016 for corresponding NZ Application No. 720667.
Office Action for corresponding Japanese application No. 2014-555720 dated Jan. 10, 2017 and English Translation thereof.
European Search Report dated Dec. 23, 2016 issued in corresponding European Application No. 16165056.9.
Australian Notice of Acceptance for Patent Application No. 2013214987 dated Jan. 24, 2017.
New Zealand First Examination Report for IP No. 627444 dated Feb. 24, 2015.
Australian Notice of Acceptance for Patent Application No. 2013214987 dated Jan. 24, 2017.
Australian Examination Report for Patent Application No. 2013214987 dated Oct. 14, 2016.
Australian Examination Report for Patent Application No. 2013214997 dated Sep. 6, 2016.
New Zealand Examination Report for IP No. 627444 dated Feb. 24, 2015.
New Zealand Examination Report for IP No. 627439 dated Feb. 24, 2015.
New Zealand First Examination Report for IP No. 720667 dated Jun. 20, 2016.
Australian Examination Report for Patent Application No. 2013214991 dated Oct. 20, 2016.
Australian Examination Report for Patent Application No. 2013214998 dated Sep. 27, 2016.
Office Action for corresponding Chinese application No. 201380017766.4 dated Feb. 17, 2017 with English translation thereof.
New Zealand First Examination Report for IP No. 714217 dated Dec. 4, 2015.
European Search Report for Application No. 16165066.8 dated Mar. 16, 2017.
Office Action for corresponding Chinese Application No. 201380007585.3 dated May 11, 2017 and English translation thereof.
European Search Report for corresponding application No. 16165071.8 dated Apr. 7, 2017.

(56)                    References Cited

OTHER PUBLICATIONS

Office Action for corresponding Chinese application No. 201380018495.4 dated Mar. 8, 2017 and English translation thereof.
Office Action for corresponding Ukranian Application No. a201409540 dated Jun. 2, 2017 and English translation thereof.
Office Action for corresponding Ukranian Application No. a201409539 dated Jun. 9, 2017 and English translation thereof.
Office Action for corresponding European Application No. 13744145.7-1664 dated Jun. 12, 2017.
Office Action for corresponding European Application No. 13744358.6-1664 dated Jun. 12, 2017.
Office Action for corresponding European Application No. 13742632.5-1664 dated Jun. 12, 2017.
Office Action for corresponding European Application No. 13744358.6 dated Jun. 12, 2017.
Office Action for corresponding European Application No. 13743475.9-1614 dated Jul. 4, 2017.
Office Action for corresponding Ukrainian Application No. a201409537 dated Jul. 25, 2017.
United States Office Action for corresponding U.S. Appl. No. 15/065,422 dated Sep. 5, 2017.
Office Action for corresponding Chinese Application No. 201380007585.3 dated Sep. 1, 2017, English translation thereof.
Office Action for corresponding Japanese Application No. 2014-555720 dated Oct. 6, 2017 and English translation thereof.
Office Action for corresponding Japanese Application No. 2014-555726 dated Oct. 5, 2017 and English translation thereof.
Office Action for corresponding European Application No. 16 165 056.9 and dated Aug. 9, 2017.
Office Action for corresponding Morrocan Application No. 37286 dated Oct. 3, 2017 and English translation thereof.
Office Action for corresponding Morrocan Application No. 37289 dated Oct. 4, 2017 and English translation thereof.
Office Action for corresponding Morroccan Application No. 37289 dated Oct. 4, 2017 and English translation thereof.
Office Action for corresponding United States U.S. Appl. No. 15/683,135 dated Nov. 9, 2017.
Office Action for corresponding European Application No. 13744145.7-1664 dated Nov. 8, 2017.
Office Action for corresponding United States U.S. Appl. No. 15/339,005 dated Sep. 28, 2017.
Office Action for corresponding Ukrainian Application No. a201409539 dated Nov. 29, 2017 and English translation thereof.
Office Action for corresponding Chinese Office Action Application No. 201380018495.4 dated Aug. 12, 2016 and English Translation thereof.
Office Action for Corresponding United States U.S. Appl. No. 13/741,267 dated Nov. 4, 2015.
Office Action for Corresponding United States U.S. Appl. No. 13/741,267 dated Mar. 9, 2016.
Office Action for Corresponding United States U.S. Appl. No. 13/741,267 dated Ocotber 6, 2016.
Office Action for Corresponding United States U.S. Appl. No. 13/741,267 dated Jan. 26, 2017.
Notice of Allowance for Corresponding United States U.S. Appl. No. 13/741,267 dated Jul. 25, 2017.
Office Action issued Mar. 15, 2018 in Malaysian Application No. PI 2014002250.
Office Action issued Apr. 26, 2018 in U.S. Appl. No. 15/911,520.
Office Action for corresponding Malaysian Application No. PI2014002168 dated Mar. 15, 2018.
Office Action for corresponding Malaysian Application No. PI2014002250 dated Mar. 15, 2018.
Office Action for corresponding Malaysian Application No. PI 2014002169 dated Mar. 30, 2018.
Re-examination Notice for corresponding Chinese Application No. 201380007585.3 dated May 21, 2018.
Office Action for corresponding U.S. Appl. No. 15/911,520 dated Aug. 9, 2018.

Final Office Action for corresponding U.S. Appl. No. 15/911,520 dated Aug. 9, 2018.
Israeli Office Action for corresponding Israeli Application No. 233885 dated Nov. 6, 2018 and English translation thereof.
U.S. Office Action dated Dec. 18, 2018 for corresponding U.S. Appl. No. 15/590,387.
"What is Vaping", Dr. Linda Richter, Center on Addiction, 2018 [online], retrieved from the Internet, [retrieved Dec. 10, 2018], <URL: https://www.centeronaddiction.org/e-cigarettes/recreational-vaping/what-vaping>. (Year: 2018).
Definition of aerosol, Merriam-Webster [online], retrieved Jun. 8, 2017, [retrieved from the Internet], <URL: https://www.merriam-webster.com/dictionary/aerosol>. (Year: 2017).
Israeli Office Action for corresponding Israeli Application No. 233884 dated Nov. 6, 2018 and English translation thereof.
United States Office Action for corresponding U.S. Appl. No. 15/590,456 dated Jan. 18, 2019.
Office Action for corresponding U.S. Appl. No. 15/911,520 dated Jan. 30, 2019.
Chinese Reexamination Notice for corresponding Application No. 201380017766.4 dated Jan. 28, 2019, English translation thereof.
Indian Examination Report for corresponding Application No. 6416/CHENP/2014 dated Jan. 30, 2019, English translation thereof.
Indian Examination Report for corresponding Application No. 6434/CHENP/2014 dated Mar. 13, 2019, English translation thereof.
United States Office Action for corresponding U.S. Appl. No. 15/683,135 dated Mar. 20, 2019.
European Office Action for corresponding Application No. 13744358.6-1122 dated Mar. 1, 2019.
European Office Action for corresponding Application No. 16165066.8-1122 dated Mar. 18, 2019.
Indian Office Action for corresponding Application No. 5797/CHENP/2014 dated Apr. 5, 2019.
United States Notice of Allowance for corresponding U.S. Appl. No. 15/590,456 dated May 8, 2019.
Final Office Action for corresponding U.S. Appl. No. 15/911,520 dated May 13, 2019.
European Office Action for corresponding Application No. 16165056.9-1122, dated May 14, 2019.
European Office Action for corresponding Application No. 13743632.5-1122, dated May 15, 2019.
Malaysian Substantive Examination Adverse Report for corresponding Application No. PI2014002169 dated Jun. 13, 2019.
United States Office Action for U.S. Appl. No. 15/911,520, dated Nov. 21, 2019.
United States Notice of Allowance for U.S. Appl. No. 15/590,456, dated May 8, 2019.
United States Office Action for U.S. Appl. No. 15/857,836, dated Feb. 6, 2020.
United States Final Office Action for U.S. Appl. No. 15/911,520, dated Apr. 13, 2020.
United States Office Action for U.S. Appl. No. 15/911,520, dated Apr. 13, 2020.
United States Notice of Allowance for U.S. Appl. No. 15/857,836, dated May 18, 2020.
United States Notice of Allowance for U.S. Appl. No. 15/911,520, dated Aug. 5, 2020.
Non-Final Office Action issued Sep. 24, 2020 in U.S. Appl. No. 16/784,357.
Communication pursuant to Article 94(3) EPC issued Oct. 16, 2020 in European Application No. 13 743 632.5.
European Office Action dated Oct. 21, 2020 for corresponding European Application No. 16165056.9.
European Examination Report dated Nov. 12, 2020 for corresponding European Application No. 16165066.8.
Israeli Official Notification dated Dec. 27, 2020 for corresponding Israeli Application No. 274421, and English-language translation thereof.
Israeli Official Notification dated Dec. 27, 2021 for corresponding Israeli Application No. 274419, and English-language translation thereof.
U.S. Office Action dated Oct. 29, 2021 for corresponding U.S. Appl. No. 16/784,357.

(56) References Cited

OTHER PUBLICATIONS

U.S. Office Action dated Feb. 3, 2022 for corresponding U.S. Appl. No. 16/784,357.
U.S. Office Action dated Mar. 24, 2022 for corresponding U.S. Appl. No. 17/084,003.
U.S. Notice of Allowance dated Jul. 1, 2022 for corresponding U.S. Appl. No. 17/084,003.
European Communication dated Jun. 24, 2022 for corresponding European Application No. 16165056.9.
Extended European Search Report dated Oct. 7, 2022 for corresponding European Application No. 22179927.3.
U.S. Office Action dated Jan. 23, 2023 for corresponding U.S. Appl. No. 16/784,357.
Notice of Allowance dated Apr. 5, 2023 issued in related U.S. Appl. No. 17/215,254.
Office Action dated Apr. 24, 2023 issued in related European Patent Application No. 16165056.9.
Brief Communication, "Letter from the Opponent," dated Feb. 28, 2023 issued in related European Patent Application No. 13744143.2.
Maciej L. Goniewicz, Ph.d., et al., "Nicotine Levels in Electronic Cigarettes," *Nicotine & Tobacco Research*, vol. 15, No. 1 (Jan. 2013), pp. 158-166.

"Heating element," in "Wikipedia," revision of Jan. 16, 2012, available online: https://en.wikipedia.org/w/index.php?title=Heating_element&oldid=471699392, retrieved on Apr. 28, 2023.
Post "Kanthal or Nichrome" in the "E-Cigarette Forum" of Apr. 20, 2012, available online: https://www.e-cigarette-forum.com/threads/kanthal-or-nichrome.289315/, retrieved on Apr. 28, 2023.
Screenshot of p. 1 of Post "Kanthal or Nichrome" in the "E-Cigarette Forum" of Apr. 20, 2012, available online: https://www.e-cigarette-forum.com/threads/kanthal-or-nichrome.289315/, retrieved on Apr. 20, 2023.
Notice of Opposition dated May 9, 2023 issued in related European patent application No. 13743632.5.
Office Action dated Aug. 24, 2023 issued in related U.S. Appl. No. 16/784,357.
Notice of Allowance dated Nov. 22, 2023 issued in related U.S. Appl. No. 17/970,121.
Summons to Attend Oral Proceedings dated Feb. 19, 2024 issued in related European Patent No. 2809184.
Office Action dated Sep. 19, 2024 issued in U.S. Appl. No. 17/970,135.
Examination Report dated Feb. 28, 2025 issued in European patent application No. 22179927.3.
Examination Report dated Jul. 24, 2025 issued in European patent application No. 24159503.2.
Intention to Grant dated Jan. 21, 2026 issued in European patent application No. 22179927.3.

* cited by examiner

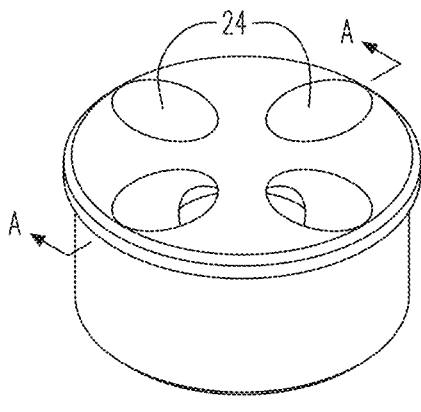
FIG. 4
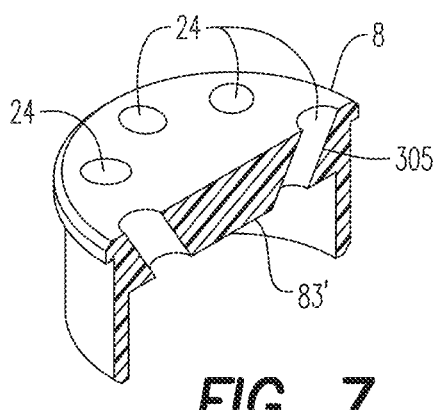
FIG. 5
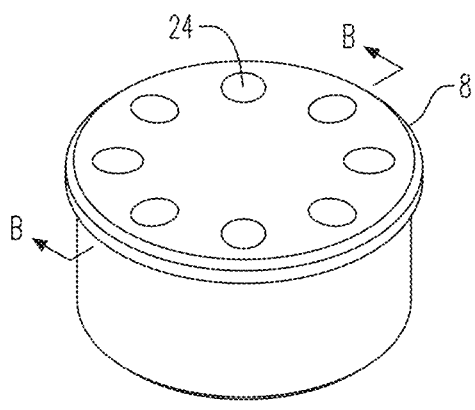
FIG. 6
FIG. 7
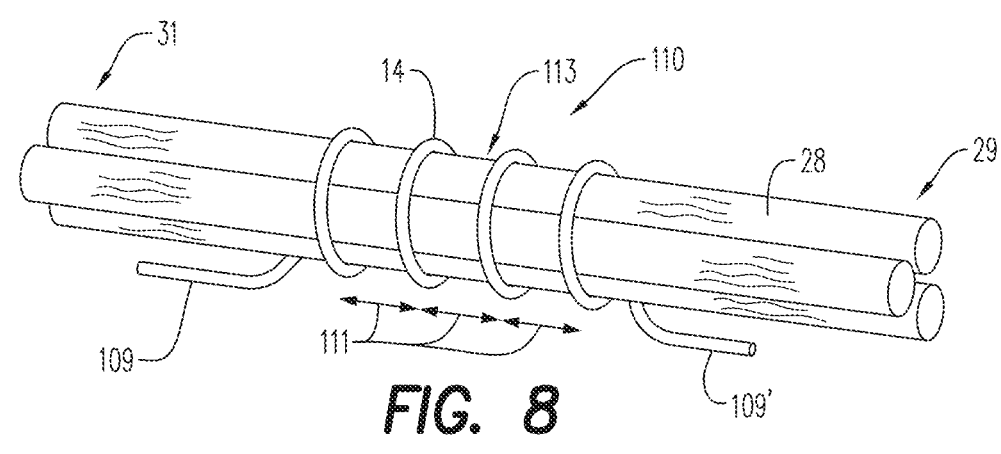
FIG. 8

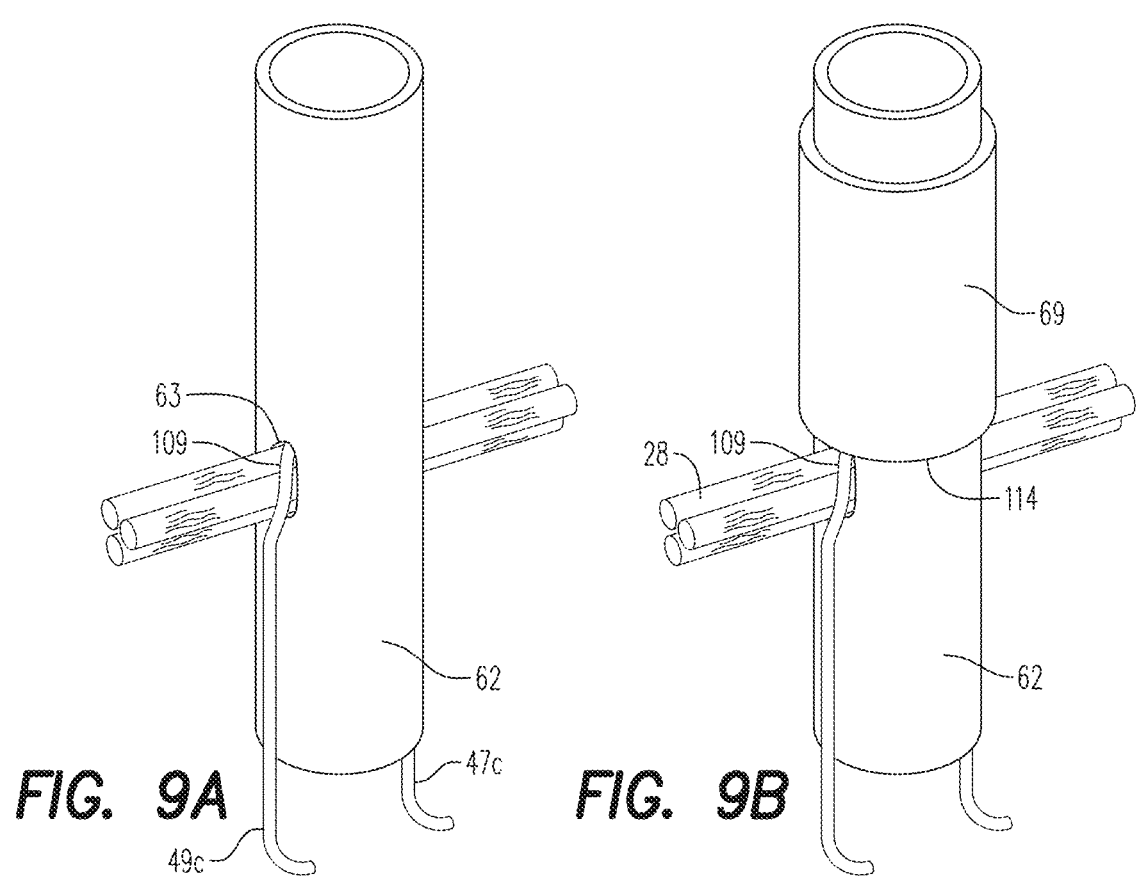
FIG. 9A
FIG. 9B
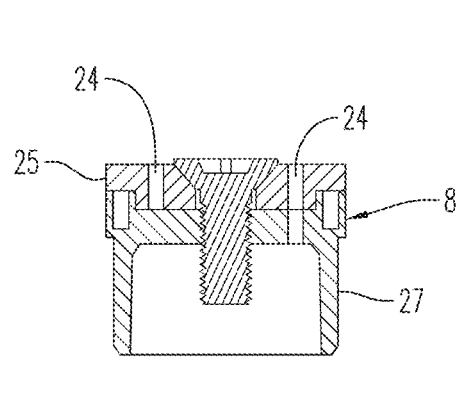
FIG. 10
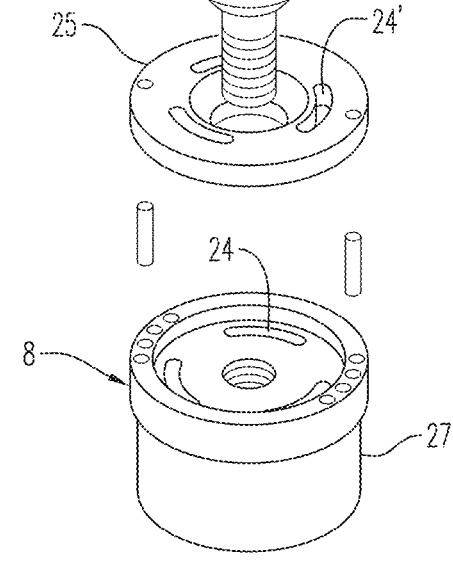
FIG. 11

ELECTRONIC CIGARETTE

CROSS REFERENCE TO RELATED APPLICATIONS

This application is a continuation of U.S. application Ser. No. 17/970,121, filed Oct. 20, 2022, which is a continuation of U.S. application Ser. No. 16/932,003, filed Jul. 17, 2020, which is a continuation of U.S. application Ser. No. 15/683, 135, filed Aug. 22, 2017, which is a continuation of U.S. application Ser. No. 15/248,116 filed on Aug. 26, 2016, which is a continuation of U.S. patent application Ser. No. 15/051,001 filed Feb. 23, 2016, which is a continuation of U.S. patent application Ser. No. 13/741,254 filed on Jan. 14, 2014, and claims priority under 35 U.S.C. § 119(e) to U.S. Provisional Application No. 61/593,004, filed on Jan. 31, 2012, the entire contents of each of which are incorporated herein by reference.

SUMMARY OF SELECTED FEATURES

An electronic cigarette or cigar (collectively "smoking article") is provided which includes a heater element which vaporizes liquid material to produce an aerosol or "vapor". The heater element preferably comprises a resistive heater coil, with a wick extending therethrough. The heater coil is constructed in a manner and formed from a material such that the production of hot spots and excessive temperatures are avoided during a puff.

The electronic article preferably includes a mouth end insert that includes at least two, diverging outlets to impart a fuller mouthfeel from the vapor output. Preferably, the aforementioned multi-ported mouth end insert cooperates with a gasket. Upon being drawn through the gasket, the vapor output enters a space just upstream of the mouthpiece which allows the air stream to expand and decelerate before entering the passages of the mouth piece insert so as to substantially avoid perceptions of "hot" at or about the lips of the "smoker".

The electronic article preferably includes a metal case portion and a precision-formed primary, air inlet port at a location along the metal case portion, preferably along a metal side wall portion of the article. The air inlet port is precision-formed within close tolerances and the air inlet port is sized so as to be the predominating source of pressure drop along an air pathway of communication between the air inlet and the source of vapor (the heater). Such arrangement assures that RTD remains essentially the same from one puff to the next and from one article to the next. To further enhance consistent performance, RTD of an article is checked in the course of its manufacture, and corrective measure undertaken, if necessary.

BRIEF DESCRIPTION OF THE DRAWINGS

FIG. 4 is a perspective view of the mouth end insert of the electronic cigarette shown in FIG. 1;

FIG. 5 is a cross-sectional view along line A-A of the mouth end insert of FIG. 4;

FIG. 6 is a perspective view of an alternative embodiment of the mouth end insert of the electronic cigarette shown in FIG. 1;

FIG. 7 is a cross-sectional view along line B-B of the mouth end insert of FIG. 6;

FIG. 8 is an enlarged detail view of the heater assembly of the electronic cigarette shown in FIG. 1;

FIG. 9A is an enlarged view of the inner tube with a heater coil and wick assembly in position prior to positioning of a closure ring;

FIG. 9B is an enlarged view of the inner tube with a heater coil and wick assembly in position after positioning of a closure ring;

FIG. 10 is a cross-sectional view of a third embodiment of a mouth end insert for use with the electronic cigarette of FIG. 1;

FIG. 11 is an exploded view of the mouth end insert of FIG. 10;

DETAILED DESCRIPTION

Electronic Cigarette Layout

Figures 1, 2, 3A, 3B:
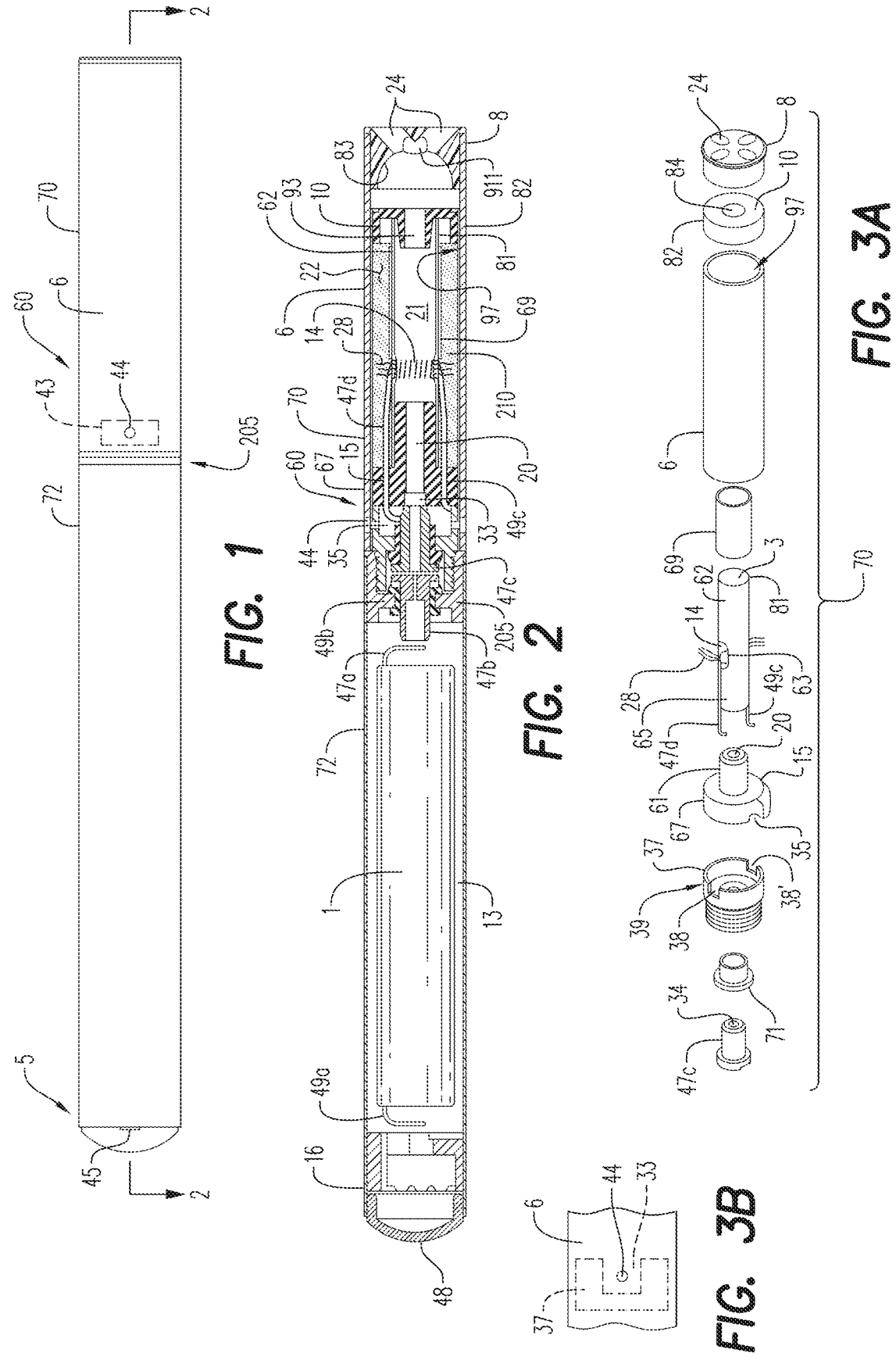
FIG. 1 is a top planar view of an electronic cigarette according to a first embodiment.
FIG. 2 is a side cross-sectional view of the electronic cigarette shown in FIG. 1.
FIG. 3a is an exploded, perspective view of elements comprising the cartridge section of the electronic cigarette shown in FIG. 1.
FIG. 3b is a detailed view of an air inlet port of the cartridge section of the electronic cigarette shown in FIG. 1.

Referring to FIGS. 1 and 2, a novel electronic cigarette (article) 60 is provided and comprises a replaceable cartridge (or first section) 70 and a reusable fixture (or second section) 72, which in the preferred embodiment are coupled together at a threaded connection 205 or by other convenience such as a snug-fit, detent, clamp and/or clasp. Generally, the second section 72 includes a puff sensor 16 responsive to air drawn into the second section 72 via an air inlet port 45 adjacent the free end or tip of the cigarette 60, a battery 1 and control circuitry. The disposable first section 70 includes a liquid supply region of 22 of liquid and a heater 14 that aerosolizes liquid that is drawn from the liquid supply region 22 through a wick 28. Upon completing the threaded connection 205, the battery 1 is connectable with the electrical heater 14 of the first section 70 upon actuation of the puff sensor. Air is drawn primarily into the first section 70 through one or more air inlets 44.

In the preferred embodiment, once the liquid of the cartridge is spent, only the first section 70 is replaced. An alternate arrangement includes a layout where the entire article 60 is disposed once the liquid supply is depleted. In such case the battery type and other features might be engineered for simplicity and cost-effectiveness, but generally embodies the same concepts as in the preferred embodiment in which the second section is reused and/or recharged.

In a preferred embodiment, the electronic cigarette 60 is about the same size as a conventional cigarette. In some embodiments, the electronic cigarette 60 can be about 80 mm to about 110 mm long, preferably about 80 mm to about 100 mm long and about 7 mm to about 8 mm in diameter. For example, in a preferred embodiment, the electronic cigarette is about 84 mm long and has a diameter of about 7.8 mm.

Preferably, at least one adhesive-backed label is applied to the outer tube 6. The label completely circumscribes the electronic cigarette 60 and can be colored and/or textured to provide the look and/or feel of a traditional cigarette. The label can include holes therein which are sized and positioned so as to prevent blocking of the air inlets 44.

The outer tube 6 and/or the inner tube 62 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene. Preferably, the material is light and non-brittle.

Cartridge Structure

Referring now to FIGS. 1, 2 and 3 the first section 70 includes an outer tube (or casing) 6 extending in a longitudinal direction and an inner tube (or chimney) 62 coaxially positioned within the outer tube 6. Preferably, a nose portion 61 (see FIG. 3a) of an upstream gasket (or seal) 15 is fitted into an upstream end portion 65 of the inner tube 62, while at the same time, an outer perimeter 67 of the gasket 15 provides a liquid-tight seal with an interior surface of the outer casing 6. The upstream gasket 15 also includes a central, longitudinal air passage 20, which opens into an interior of the inner tube 62 that defines a central channel 21. A transverse channel 33 at a backside potion of the gasket 15 intersects and communicates with the central channel 20 of the gasket 15. This channel 33 assures communication between the central channel 20 and a space 35 (see FIG. 2) defined between the gasket 15 and a cathode connector piece 37. In the preferred embodiment, the piece 37 includes a threaded section for effecting the threaded connection 205.

The cathode connector piece 37 includes opposing notches 38, 38' about its perimeter 39, which, upon insertion of the cathode connector piece 37 into the casing 6, are aligned with the location of each of two RTD-controlling, air inlet ports 44 and 44' in the outer casing 6. In an embodiment, such alignment may appear as shown in FIG. 3'(Detail). Such arrangement allows for placement of the ports 44, 44' close to the threaded connection 205 without occlusion by the presence of the cathode connector piece 37. The arrangement also reinforces the area of ports 44, 44' to facilitate precise drilling of the holes 44, 44'.

Air Inlets and Control of Resistance to Draw

In the preferred embodiment, at least one air inlet 44 is formed in the outer tube 6, preferably adjacent the threaded connection 205 to minimize the chance of a smoker' fingers occluding one of the ports and to control the resistance to draw (RTD) during smoking. Preferably, each of the RTD controlling, air inlets 44 and 44' are machined into the casing 6 with precision tooling such that their diameters are closely controlled and replicated from one cigarette 60 to the next during their manufacture. Preferably, the air inlets 44 and 44' are drilled with carbide drill bits or other high-precision tools and/or techniques. Also preferably, the outer tube 6 is formed of metal or metal alloys such that the size and shape of the air inlets 44, 44' is not altered during manufacturing operations, packaging and smoking. Thus, the air inlets 44, 44' provide consistent RTD. In the preferred embodiment, the air inlets 44, 44' are sized and configured such that the electronic cigarette 60 has a RTD in the range of from about 60 mm $H_2O$ to about 150 mm $H_2O$, more preferably about 90 mm $H_2O$ to about 110 mm $H_2O$, most preferably about 100 mm $H_2O$ to about 130 mm $H_2O$.

The RTD controlling, air inlets 44 and 44' are the critical orifice (i.e. the smallest orifice along the pathway from the air inlets 44, 44' and the inner passage 21 of the inner tube 62 (where the heater 14 aerosolizes liquid). Accordingly, the air inlets 44 and 44' control the level of resistance to draw of the cigarette 60, which may be set at a level that contributes a drawing experience similar to that of drawing upon a conventional, lit-end cigarette.

Referring specifically to FIG. 1, another aspect of maintaining precise and reproducible resistance to draw is use of a metallic material in the casing 6 which is conducive to precision tooling and techniques. If another material is desired for the casing 6 (such as a plastic for presenting a softer feel), the air inlets 44, 44' may be instead formed in a metallic plate fixture (or insert) 43 provided at the location of the air inlets 44, 44' so as to maintain the precision of the air inlets 44, 44'.

It is envisioned that the metallic plate insert 43 may be included even in instances where the casing 6 is metallic, in that such arrangement allows the air inlets 44, 44' to be produced and tested separately (off-line) on a collection of blank metallic plate inserts 43. Advantageously, should any finished metallic plate inserts 43 fail to meet standards or specifications for air inlet diameter (and RTD), the failed inserts may be disposed of instead of entire cartridge assemblies (first section) 70.

Referring back to FIG. 1, the metallic plate insert 43 may comprise a separate piece that becomes affixed to an outer surface of the casing 6 or wholly within the casing 6, in which case the outer casing 6 is preferably provided with an oversized hole, which can be superposed over the area of the air inlet 44. It is also envisioned that the insert might be shaped and fitted flush with the contour of the casing 6, using a snap fit and/or adhesive between the insert and the casing 6 or entirely within (internal of the outer casing 6). Preferably the shape and the location of the air inlet 44 of the insert 43 has a symmetry such that the air inlet 44 remains fully operative whether the insert 43 is positioned as shown in FIG. 1 or flipped 180 degrees. Moreover, the metallic plate insert 43 can be provided on an inside surface or on an outside surface of the outer casing 6. The metallic plate insert 43 can extend fully or partially about a circumference of the cigarette 60. When the metallic plate insert 43 extends partially about the circumference, multiple metallic plate inserts 43 can be used, each metallic plate insert 43 corresponding to a single air inlet 44, 44'.

In the preferred embodiment, the second section 72, includes an air inlet 45 at an upstream end 5 of the cigarette 60, which is sized just sufficient to assure proper operation of the puff sensor 16, located nearby. Drawing action upon the mouth end insert 8 is communicated to the air inlet port 45 through central channels provided in the anode post 47c of the first section 70 and the anode connection post 47b of the second section 72 and along space 13 between the battery 1 and the casing of the second section 72. These channels and the port 45 itself are sized such that the airflow rate there through are much smaller than through the air inlets 44, 44', so that the impact on RTD is minimized and consistency in RTD is maintained. For example, each air inlet can be less than about 2.0 mm in width and less than about 1.5 mm in depth. For example, each air inlet can be about 0.7 mm to about 0.8 mm in width and about 0.7 mm to about 0.8 mm in depth. In a preferred embodiment, 95% of the air introduced in the cigarette 60 is through the air inlets 44, 44', whereas only 5% of the total air flow enters through the inlet 45 at the upstream end 5 of the cigarette 60. Preferably, the ratio is determined by making a central channel 34 of the anode post 47b of the second section 72 small enough to impart a pressure drop far greater than that of the air inlets 44, 44'. For example, the central channel 34 of the anode post 47b may be sized to impart a pressure drop of approximately 2000 mm water (in contrast to a nominal pressure drop of 100 mm water from air inlets 44, 44' combined).

Figure 19:
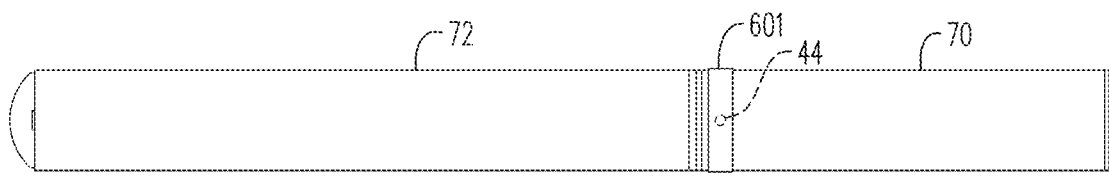
FIG. 19 is a side-view of an electronic cigarette according to another embodiment.

Referring to FIG. 19, in order to maintain consistent RTD in the product, a removable protective covering 601 can be applied to the air inlets 44, 44' to prevent degradation from dirt and dings during, manufacture, packaging shipping and handling at retail and beyond as shown in FIG. 19. To maintain consistent RTD until consumption, a circumferential wrapping or tape 601 may be wrapped about the outer casing 6 at the locations of the air inlets 44, 44'. In the alternative or in addition, the cigarette 60 may be accompanied with a reusable protective cover to provide the same or additional protections.

In addition, current manufacturing techniques for electronic cigarettes can be modified to include testing for consistent RTD. In other words, there is a need to couple an understanding of how to achieve consistent RTD in the product (as taught above) with an understanding of how to test for it in the course of manufacturing the product (as taught in the following). Achieving consistent RTD from one electronic cigarette to the next promotes consistent performance and delivery levels, and enhances smoking experiences by meeting smoker's expectations that a draw upon an electronic cigarette will be akin to drawing upon a lit end cigarette or cigar. The latter may include testing metallic plate inserts 43 prior to installation as previously described; or instead or in addition, testing completed first sections 70 by fastening a nominal, but inactivated second section 72 to a newly produced first section 70 to create a benign, inactive test configuration that accurately reproduces airflow event, but without risk of heater activation and applying a predetermined drawing action upon the configuration while measuring pressure drop. By way of non-limiting example, a fully assembled electronic cigarette may be drawn through the test configuration while pressure drop is measured using a PV10 pressure drop instrument manufactured by Borgwaldt KC of Chesterfield, Virginia. A suitable pressure drop testing method for electronic cigarettes can be adopted from standard method ISO 6565:2011 entitled "Tobacco and tobacco products—Draw Resistance of Cigarettes and Pressure Drop of Filter Rods—Standard Conditions and Measurement", and applied with instrumentation capable of measure pressure drop in a working range of 50 mmWG (mm water gauge) to 1900 mmWG and a diameter range of 5.0 mm to 9.0 mm. The test can be completed in a matter of seconds and the instrumentation can be calibrated to a range of 50 mmWG to 300 mmWG.

Instead of using an inactivated second section 72, it is envisioned that a releasable test body might be employed to serve the same purpose in a benign (inactive) test configuration. The test body would be configured to reproduce nominal impact of a real reusable second portion 72 upon RTD, but could be optimized for machine handing and high speed automated coupling to and removal from newly produced first sections 70 that are undergoing testing.

Figure 12:
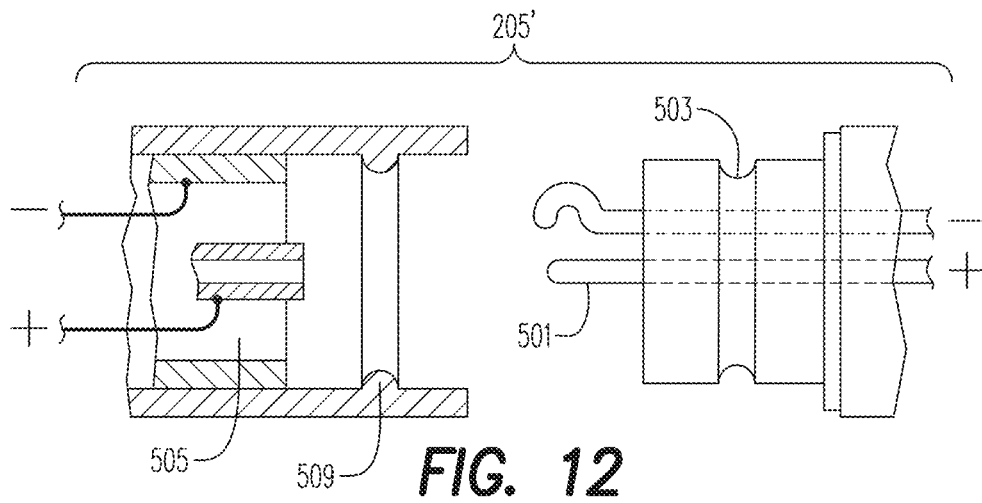
FIG. 12 is a detailed view of an alternative connection arrangement assembly for use with the electronic cigarette of FIG. 1.

The inclusion of a threaded connection 205 does not facilitate automated, high speed machine handling and execution of the RTD tests. Referring now to FIG. 12, an alternative coupling 205' may include connections comprising pins 501 and releasable detents 503 and/or electrical bearing surfaces 505 with releasable detents, rotational locking devices or the like. In the illustrated embodiment, the detent 503 cooperates with a raised annulus 509. In the alternative, one or more biased balls may be used in lieu of or in addition to the raised annulus 509. Such arrangements facilitate automated machine handling, provide a greater capacity for speedy yet accurate testing of RTD, and facilitate machine automated execution of RTD testing. It is envisioned that quality control during the drilling of orifices could include a feedback loop such that the RTD test results are monitored to detect trends away from specifications so that corrective measures may be undertaken, such as replacement of a worn drill bit.

Referring now to FIGS. 3a and 3b, preferably, the cathode connector piece 37 includes opposing notches 38, 38' about its perimeter 39, which, upon insertion of the cathode connector piece 37 into the outer casing 6, are aligned with the location of each of two or more RTD-controlling, air inlets 44 and 44' in the outer casing 6. In some embodiments, more than two air inlets 44, 44' may be included (e.g., three, four, five, six, seven, eight, nine, ten or more). Alternatively, a single air inlet 44 can be included. In an embodiment, such alignment may appear as shown in FIG. 3b. Such arrangement allows for placement of the air inlets 44, 44' close to the threaded connection 205 without occlusion by the presence of the cathode connector piece 37. The arrangement also reinforces the area of air inlets 44, 44', which can serve to facilitate precise drilling of the air inlets 44, 44'. Other arrangements can also be used as discussed below.

Figure 13:
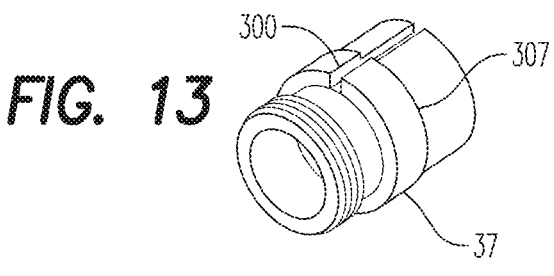
FIG. 13 is a second embodiment of a connector cathode including a notch.

In another embodiment, as shown in FIG. 13, the cathode connector piece 37 can include one or more slits 300 formed in the perimeter 39 of the cathode connector piece 37. The outer casing 6 of the cartridge portion 70 is slid over the unthreaded end of the connector piece 37 until it reaches the stop (or edge) 307, leaving a predetermined portion of the slit 300 open to the exterior of the cartridge portion 70 for the admission of air. The admitted air can travel along the slit 300 and into the interior of the cartridge portion 70. The slit 300 may be used as the critical orifice and can be used in lieu of air inlets 44 and 44'. In another embodiment, the slit 300 may be used in addition to air inlets 44 and 44'.

Figure 14A:
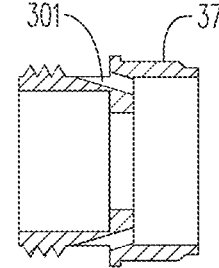
FIGS. 14A, 14B and 14C illustrate a third embodiment of a connector cathode including angled holes.
Figure 14B:
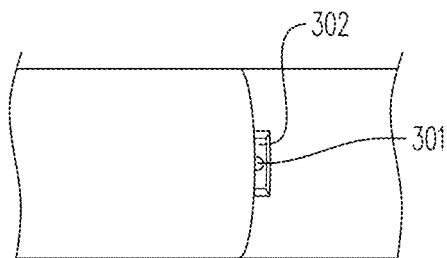
Figure 14C:
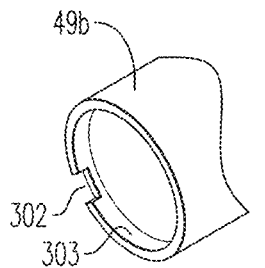

In yet another embodiment, as shown in FIGS. 14A, 14B and 14C, the cathode connector piece 37 can include one or more angled holes 301 formed therein, which communicate with one or more slots 302 in a cathode connection fixture 49b. Preferably, the cathode connection fixture 49b can include an empty annular space 303 in an inner portion thereof which communicates with the one or more slots 302. Air is drawn in through slot 302 and travels into the annular space 303 and from there into the angled holes 307. Thus, there is no need to line up the slot 302 with the angled hole 301 because air will travel around the annular space 303 and into the angled holes 301 even if the holes 301 and slots 302 are not aligned. This arrangement provides advantages during manufacture since the angled holes 301 need not be aligned with the slots 302.

Figure 15:
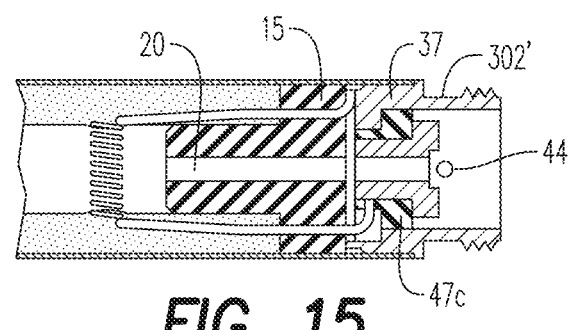
FIG. 15 is an illustration of a connector cathode and anode in which the anode is shortened to allow communication with air inlets.
Figure 16:
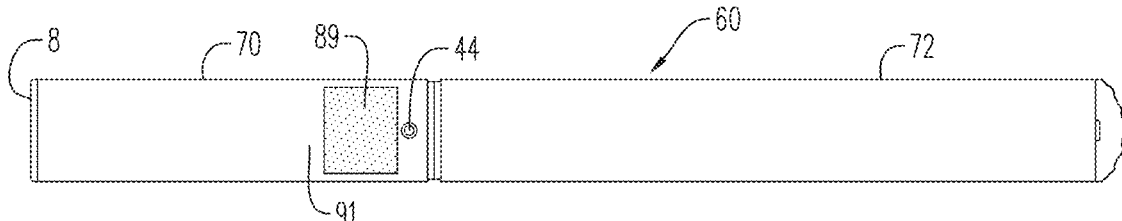
FIG. 16 is a top view of an electronic cigarette including an aroma strip on an outer surface thereof.

As shown in FIG. 15, in yet another embodiment, the anode post 47c can be shortened as compared to the anode post 47c of FIG. 2 so as to provide a larger air gap behind the cathode connector piece 37. Air enters via slot 302' (not shown in FIG. 15 other than its relative position) and is drawn through an internal air inlet 44 via annular space 303 and then flows straight into the air gap, through the central channel 34 of the anode post 47c and into the central channel 20 leading to the heater 14.

Liquid Supply Region, Heater and Wick

Preferably, a nose portion 93 of an downstream gasket 10 is fitted into a downstream end portion 81 of the inner tube 62. An outer perimeter 82 of the gasket 10 provides a substantially liquid-tight seal with an interior surface 97 of the outer casing 6. The downstream gasket 10 includes a central channel 84 disposed between the central passage 21 of the inner tube 62 and the interior of the mouth end insert 8 and which communicates aerosol from the central passage 21 to the mouth end insert 8.

The space defined between the gaskets 10 and 15 and the outer tube 6 and the inner tube 62 establish the confines of a liquid supply region 22. The liquid supply region 22 comprises a liquid material and optionally a liquid storage medium 210 operable to store the liquid material therein. The liquid storage medium 210 may comprise a winding of cotton gauze or other fibrous material about the inner tube 62.

In the preferred embodiment, the liquid supply region 22 is contained in an outer annulus 620 between inner tube 62 and outer tube 6 and between the gaskets 10 and 15. Thus, the liquid supply region 22 at least partially surrounds the central air passage 21. The heater 14 extends transversely across the central channel 21 between opposing portions of the liquid supply region 22.

Preferably, the liquid storage medium 210 is a fibrous material comprising cotton, polyethylene, polyester, rayon and combinations thereof. Preferably, the fibers have a diameter ranging in size from about 6 microns to about 15 microns (e.g., about 8 microns to about 12 microns or about 9 microns to about 11 microns). The liquid storage medium 210 can be a sintered, porous or foamed material. Also preferably, the fibers are sized to be irrespirable and can have a cross-section which has a y shape, cross shape, clover shape or any other suitable shape. In the alternative, the liquid supply region 22 may comprise a filled tank lacking a fibrous storage medium 21 and containing only liquid material.

Also preferably, the liquid material has a boiling point suitable for use in the electronic cigarette 60. If the boiling point is too high, the heater 14 will not be able to vaporize liquid in the wick 28. However, if the boiling point is too low, the liquid may vaporize even when the heater 14 is not being activated.

Preferably, the liquid material includes a tobacco-containing material including volatile tobacco flavor compounds which are released from the liquid upon heating. The liquid may also be a tobacco flavor containing material or a nicotine-containing material. Alternatively, or in addition, the liquid may include a non-tobacco material. For example, the liquid may include water, solvents, ethanol, plant extracts and natural or artificial flavors. Preferably, the liquid further includes an aerosol former. Examples of suitable aerosol formers are glycerine and propylene glycol.

Referring now also to FIG. 8, in use, liquid material is transferred from the liquid supply region 22 and/or liquid storage medium 210 in proximity of the 14 heater by capillary action of the wick 28. In one embodiment, the wick 28 has a first end portion 29 and a second end portion 31 as shown in FIG. 8. The first end 29 and the second end 31 extend into opposite sides of the liquid storage medium 21 for contact with liquid material contained therein. Also preferably, the heater 14 at least partially surrounds a central portion 113 of the wick 28 such that when the heater 14 is activated, the liquid in the central portion 113 of the wick 28 is vaporized by the heater 14 to form an aerosol. The wick 28 preferably comprises filaments having a capacity to draw a liquid, more preferably a bundle of glass (or ceramic) filaments and most preferably a bundle comprising a group of windings of glass filaments, preferably three of such windings, all which arrangements are capable of drawing liquid via capillary action via interstitial spacings between the filaments. Preferably, the wick 28 is flexible and includes three strands, each strand including a plurality of filaments. Moreover, it is noted that the end portions of the 29 and 31 of the wick 28 are flexible and foldable into the confines of the liquid supply region 22.

Advantageously, the liquid material in the liquid supply region 22 is protected from oxygen (because oxygen cannot generally enter the liquid supply region 22 via the wick 28). In some embodiments, the liquid material is also protected from light so that the risk of degradation of the liquid material is significantly reduced. Thus, a high level of shelf-life and cleanliness can be maintained.

In the preferred embodiment, the liquid supply region 22 is sized and configured to hold enough liquid material such that the electronic cigarette 60 is operable for smoking for at least about 200 seconds, preferably at least about 250 seconds, more preferably at least 300 seconds and most preferably at least about 350 seconds. Thus, liquid supply region 22 is equivalent to about one pack of traditional cigarettes. Moreover, the electronic cigarette 60 can be configured to allow each puff to last a maximum of about 5 seconds.

Mouth End Insert

Referring to FIGS. 2, 3a, 4, 5, 6, 7 and 17, the first section 70 includes a mouth end insert 8 having at least two diverging outlet passages 24 (e.g., preferably 2 to 6 outlet passages 24, more preferably 4 outlet passages 24). Preferably, the outlet passages 24 are located off-axis and are angled outwardly in relation to the central channel 21 of the inner tube 62 (i.e., divergently). Also preferably, the mouth end insert (or flow guide) 8 includes outlets 24 uniformly distributed about the perimeter of mouth end insert 8 so as to substantially uniformly distribute aerosol in a smoker's mouth during use and create a greater perception of fullness in the mouth. Thus, as the aerosol passes into a smoker's mouth, the aerosol enters the mouth and moves in different directions so as to provide a full mouth feel. In contrast, electronic cigarettes having a single, on-axis orifice tend to direct its aerosol as single jet of greater velocity toward a more limited location within a smoker's mouth.

In addition, the diverging outlet passages 24 are arranged and include interior surfaces 83 such that droplets of unaerosolized liquid material, if any, that may be entrained in the aerosol impact the interior surfaces 83 of the mouth end insert 8 and/or impact portions of walls 305 which define the diverging outlet passages 24. As a result such droplets are substantially removed or broken apart, to the enhancement of the aerosol.

In the preferred embodiment, the diverging outlet passages 24 are angled at about 5° to about 60° with respect to the longitudinal axis of the outer tube 6 so as to more completely distribute aerosol throughout a mouth of a smoker during use and to remove droplets. In a preferred embodiment, there are four diverging outlet passages 24 each at an angle of about 40° to about 50° with respect to the longitudinal axis of the outer tube 6, more preferably about 40° to about 45° and most preferably about 42°.

Preferably, each of the diverging outlet passages 24 has a diameter ranging from about 0.015 inch to about 0.090 inch (e.g., about 0.020 inch to about 0.040 inch or about 0.028 inch to about 0.038 inch). The size of the diverging outlet passages 24 and the number of diverging outlet passages 24 can be selected to adjust the resistance to draw (RTD) of the electronic cigarette 60, if desired.

Figure 17:
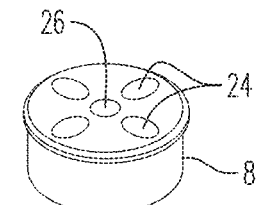
FIG. 17 is a perspective view of a fourth embodiment of a mouth end insert for use with the electronic cigarette.

In one embodiment shown in FIG. 17, the mouth end insert 8 can include diverging outlet passages 24 and an on-axis outlet passage 26.

As shown in FIG. 2, an interior surface 83 of the mouth end insert 8 can comprise a generally domed surface 83. Alternatively, as shown in FIG. 7, the annular interior surface 83' of the mouth end insert 8 can be generally cylindrical or frustoconical, with a planar end surface. Preferably, the interior surface 83 is substantially uniform over the surface thereof. Moreover, the interior surface 83 can be symmetrical about the longitudinal axis of the mouth end insert 8. However, in other embodiments, the interior surface 83 can be irregular and/or have other shapes.

In a preferred embodiment, a hollow 911 is disposed at the convergence of the diverging outlet passages 24 within the mouth end insert 8

The mouth end insert 8 may be integrally affixed within the tube 6 of the cartridge 70.

As mentioned previously, the multi-port mouth end insert 8 disperses and changes the direction of the aerosol as it is drawn from the electronic cigarette 60 so as to provide a fuller mouth feel. As aerosol is formed, it passes through the central channel 21 in the inner tube 62 and through the central channel 84 in the downstream gasket 10. In panel testing of early prototypes, some panelists reported a "hot" sensation on the lips from smoking an electronic cigarette constructed to include a mouth end insert including a plurality of diverging outlet passages 24 and a central channel 84 having a diameter of about 1.3 mm. However, in electronic cigarettes in which the inside diameter of the central channel 84 was increased to about 2.6 mm, reports of "hot" sensations essentially ceased.

Dynamic modeling of the area at and about the downstream gasket 10 and the mouth end insert 8 has indicated that a small 1 mm wide central channel 84 at the gasket 10 tends to create peak velocities of approximately 12 meters per second (m/sec) in aerosol exiting the mouth end insert. In contrast, modeling of a system including a 5 mm wide central channel 84 indicates peak velocities of only 2.5 m/s is achieved at the exits of the diverging outlet passages 24 of the mouth end insert 8, which is approximately a five-fold decrease in air velocity. From the aforementioned testing and modeling it is believed a further improvement in the organoleptic experience with an electronic cigarette is achieved by preventing acceleration of the aerosol flow stream by increasing the diameter of the central channel 84 before it is drawn through the exits of the diverging outlet passages 24 of the multi-port mouth end insert 8.

Accordingly, it is advantageous to provide an electronic cigarette having a downstream gasket 10 having a central channel 84, which has a diameter sufficient to prevent acceleration of the aerosol flow stream before reaching the mouth end insert 8. Preferably, the diameter of the central channel 84 is about 2.0 mm to about 3.0 mm, more preferably about 2.4 mm to about 2.8 mm. The mouth end insert 8 then divides output from the central channel 84 into multiple divergent streams of reduced speed so as to provide a full mouth feel and to avoid sensations of "hot".

In that an appropriately sized central channel 84 of the gasket 10 serves to substantially prevent acceleration of the aerosol, such functionality can be further enhanced by providing the exit orifice with a beveled rim (not shown) at its exit plane to further reduce speed of the aerosol before it reaches the mouth end insert 8.

In an alternative embodiment, the mouth end insert 8 and the downstream gasket 10 can be integrally formed as a single piece so as to enhance consistent performance and to facilitate manufacture.

As shown in FIGS. 10 and 11, in an alternative embodiment, the electronic cigarette 60 of FIG. 1 can include a mouth end insert 8 having a stationary piece 27 and a rotatable piece 25. Outlets 24, 24' are located in each of the stationary piece 27 and the rotatable piece 25. The outlets 24, 24' match up as shown to allow aerosol to enter a smoker's mouth. However, the rotatable piece 25 can be rotated within the mouth end insert 8 so as to at least partially block one or more of the outlets 24 in the stationary mouth end insert 28. Thus, the consumer can adjust the amount of aerosol drawn with each puff. The outlets 24, 24' can be formed in the mouth end insert mouth end insert 8 such that the outlets 24, 24' diverge to provide a fuller mouth feel during inhalation of the aerosol.

Circuitry, Alloys Improving Consistent Heater Performance, Hot Spots and Carbonyl Abatement In the preferred embodiment, the power supply 1 includes a battery arranged in the electronic cigarette 60 such that the anode 47a is downstream of the cathode 49a. A battery anode post 47b of the second section 72 preferably contacts the battery anode 47a.

More specifically, electrical connection between the anode 47a of the battery 1 and the heater coil 14 in the first section 70 is established through a battery anode connection post 47b in the second section 72 of the electronic cigarette 60, an anode post 47c of the cartridge 70 and an electrical lead 47d connecting a rim portion of the anode post 47c with an electrical lead 109 of the heater element 14 (see FIG. 8). Likewise, electrical connection between the cathode 49a of the battery 1 and the other lead 109' of the heater coil 14 is established through the threaded connection 205 between a cathode connection fixture 49b of the second portion 72 and the cathode connector piece 37 of the first section 70 and from there through an electrical lead 49c which electrically connects the fixture 37 to the opposite lead 109' of the heater coil 14.

Preferably, the electrical leads 47d, 49c and the heater leads 109, 109' are highly conductive and temperature resistant while the coiled section 110 of the heater 14 is highly resistive so that heat generation occurs primarily along the coils 110 of the heater 14. Also preferably, the electrical lead 47d is connected to the heater lead 109 by crimping. Likewise, the electrical lead 49c is connected to the heater lead 109' by crimping. In an alternative embodiment, the electrical leads 47d, 49c can be attached to the heater leads 109, 109' via soldering. Crimping is preferred as it speeds manufacture.

The battery can be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, preferably, the electronic cigarette 60 is usable by a smoker until the energy in the power supply is depleted or in the case of lithium polymer battery, a minimum voltage cut-off level is achieved.

Alternatively, the power supply 1 may be rechargeable and include circuitry allowing the battery to be chargeable by an external charging device. In that case, preferably the circuitry, when charged, provides power for a pre-determined number of puffs, after which the circuitry must be re-connected to an external charging device. To recharge the electronic cigarette 60, an USB charger or other suitable charger assembly can be used.

Preferably, the electronic cigarette 60 also includes control circuitry including a puff sensor 16. The puff sensor 16 is operable to sense an air pressure drop and initiate application of voltage from the power supply 1 to the heater 14. As shown in FIG. 2, the control circuitry can also include a heater activation light 48 operable to glow when the heater 14 is activated. Preferably, the heater activation light 48 comprises an LED and is at an upstream end of the electronic cigarette 60 so that the heater activation light 48 takes on the appearance of a burning coal during a puff. Moreover, the heater activation light 48 can be arranged to be visible to the smoker. In addition, the heater activation light 48 can be utilized for cigarette system diagnostics or to indicate that recharging is in progress. The light 48 can also be configured such that the smoker can activate and/or deactivate the light 48 for privacy, such that the light 48 would not activate during smoking if desired.

Preferably, the at least one air inlet 45 (FIG. 1) is located adjacent the puff sensor 16, such that the puff sensor 16 senses air flow indicative of a smoker taking a puff and activates the power supply 1 and the heater activation light 48 to indicate that the heater 14 is working.

A control circuit is preferably integrated with the puff sensor 16 and supplies power to the heater 14 responsive to the puff sensor 16, preferably with a maximum, time-period limiter.

Alternatively, the control circuitry may include a manually operable switch for a smoker to initiate a puff. The time-period of the electric current supply to the heater may be pre-set depending on the amount of liquid desired to be vaporized. Alternatively, the circuitry may supply power to the heater 14 as long as the puff sensor 16 detects a pressure drop.

Preferably, when activated, the heater 14 heats a portion of the wick 28 surrounded by the heater for less than about 10 seconds, more preferably less than about 7 seconds. Thus, the power cycle (or maximum puff length) can range in period from about 2 seconds to about 10 seconds (e.g., about 3 seconds to about 9 seconds, about 4 seconds to about 8 seconds or about 5 seconds to about 7 seconds).

Preferably, the heater 14 is a wire coil that surrounds the wick 28. Examples of suitable electrically resistive materials include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel. For example, the heater can be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. Preferably, the heater 14 comprises at least one material selected from the group consisting of stainless steel, copper, copper alloys, nickel-chromium alloys, super alloys and combinations thereof. In a preferred embodiment, the heater 14 is formed of nickel-chromium alloys or iron-chromium alloys, although the latter is not preferred for reasons which follow.

In another embodiment, the heater 14 can be a ceramic heater having an electrically resistive layer on an outside surface thereof.

In another embodiment, the heater 14 may be constructed of an iron-aluminide (e.g., FeAl or $Fe_3Al$), such as those described in commonly owned U.S. Pat. No. 5,595,706 to Sikka et al. filed Dec. 29, 1994, or nickel aluminide (e.g., $Ni_3Al$). Use of iron-aluminide is advantageous in that iron-aluminide exhibits high resistivity. FeAl exhibits a resistivity of approximately 180 micro-ohms, whereas stainless steel exhibits approximately 50 to 91 micro-ohms. The higher resistivity lowers current draw or load on the power source (battery) 1.

In the preferred embodiment, the heater coil 14 is formed from a nickel-chromium alloy that is essentially free of iron content. Experience has indicated that heater coils constructed from an iron chromium alloy suffered oxidation of their iron content if the alloys were contacted with water during manufacturing operations, during shelf-life and/or operation of the device.

It is known that heating glycerin and/or propylene glycol beyond certain temperatures produces carbonyls (which include formaldehydes). Iron oxide tends to catalyze these reactions such that carbonyls are produced at lower temperatures. By using alloys essentially free of iron content, such catalyzation is avoided and the possibility of producing carbonyls and other constituents is minimized.

Moreover, in the manufacture and design of the preferred embodiment, certain aspects and measures are employed to avoid occurrence of unintended "hot spots" in the heater coil 14 during its heating cycle. Hot spots may contribute excessive peak temperatures that may produce undesired constituents that would otherwise be avoided in the absence of a hot spot.

While not wishing to be bound by theory, it is believed that if a winding of a coil heater 14 is altered such that spacing between loops of the coil 14 is locally reduced, the reduced spacing will create hotspots that are believed to drive peak temperatures beyond desirable levels. It is also believed that establishing uniform spacing along the coils of the heater 14 and taking steps to preserve the original, uniform spacing in the winding of the coil heater 14 will avoid the consequences of "hot spots".

In particular and referring to FIG. 8, it is envisioned that production of consistent coil spacing 111 throughout the coiled section 110 of a given heater coil 14 may be achieved in ways including using automated winders to wind the coil about the wick 28 and using the wick 28 as an arbor for the winding step. In the preferred embodiment 3 to 8 windings are preferred, more preferably, 3 to 5 windings.

Once established, the uniformity of the coil spacing 111 is preserved in the course of manufacture and in the design of the preferred embodiment.

Referring also to FIG. 9A, in particular, the provision of opposing slots 63 in the inner tube 62 facilitates placement of the heater 14 and wick 28 into position within the inner tube 62 without impaction between edges of the slots 63 and the coiled section 110 (shown in FIG. 8) of the heater 14. Accordingly, edges of the slots 63 are not allowed to impact and alter the coil spacing 111 of the heater 14, which would otherwise create potential sources of hotspots.

Referring now to FIG. 9B, care is taken to position a closure ring 69 such that it is proximate to or touches but does not urge against the wick 28. Such positioning avoids imposing bending moments upon the heater coil 14 and avoids bowing of the coil 14 which might otherwise produce hotspots along one side of the coil 14 where the coil spacing 111 would become compressed and reduced. Thus, the upstream edge 114 of the closure ring 69 is brought into proximity of the wick 28, but is not positioned over the wick 28 so as to avoid the possibility of the aforementioned bowing effect. The closure ring 69, when placed as shown in FIG. 9B, closes off a remainder of open space provided between the heater coil assembly and the slot 63.

In the preferred embodiment, the inner tube 62 and the closure ring 69 are constructed from woven fiberglass.

In the preferred embodiment, the inner tube 62 has a diameter of about 4 mm and each of the opposing slots 63 has major and minor dimensions of about 2 mm by about 4 mm.

In one embodiment, the heater 14 comprises a wire coil which at least partially surrounds the wick 28. In that embodiment, preferably the wire is a metal wire and/or the heater coil may extend fully or partially along the length of the wick 28. The heater coil 14 may extend fully or partially around the circumference of the wick 28. In another embodiment, the heater coil is not in contact with the wick 28.

Preferably, the heater 14 heats liquid in the wick 28 by thermal conduction. Alternatively, heat from the heater 14 may be conducted to the liquid by means of a heat conductive element or the heater 14 may transfer heat to the incoming ambient air that is drawn through the electronic cigarette 60 during use, which in turn heats the liquid by convection.

In one embodiment, the wick 28 comprises a ceramic wick of ceramic filaments having a capacity to draw a liquid. As noted above, the wick 28 is at least partially surrounded by the heater 14. Moreover, in the preferred embodiment, the wick 28 extends through opposed slots 63 in the inner tube 62 such that each end of the wick 28 is in contact with the liquid supply region 22 (shown in FIG. 2).

In the preferred embodiment, the wick 28 comprises filaments and comprises a bundle of glass filaments. For example, the wick 28 may include a plurality of filaments. The filaments or threads may be generally aligned in a direction perpendicular (transverse) to the longitudinal direction of the electronic cigarette. Preferably, the wick 28 includes 1 to 8 filaments, more preferably 2 to 6 filaments. In the preferred embodiment, the wick 28 includes 3 stands, each strand comprising a plurality of glass filaments twisted together.

In the preferred embodiment, the structure of the wick 28 is formed of filaments through which the liquid can be transported to the heater 14 by capillary action. The wick 28 can include filaments having a cross-section which is generally cross-shaped, clover-shaped, Y-shaped or in any other suitable shape.

Preferably, the wick 28 includes any suitable material or combination of materials. Examples of suitable materials are glass, ceramic- or graphite-based materials. Moreover, the wick 28 may have any suitable capillarity drawing action to accommodate aerosol generating liquids having different liquid physical properties such as density, viscosity, surface tension and vapor pressure. The capillary properties of the wick 28, combined with the properties of the liquid, ensure that the wick 28 is always wet in the area of the heater 14 to avoid overheating of the heater 14.

Instead of using a wick 28, the heater 14 can be a porous material which incorporates a resistance heater formed of a material having a high electrical resistance capable of generating heat quickly.

Preferably, the wick 28 and the fibrous medium of the liquid supply region 22 are constructed from glass fiber.

Sleeve Assembly

Figure 18:
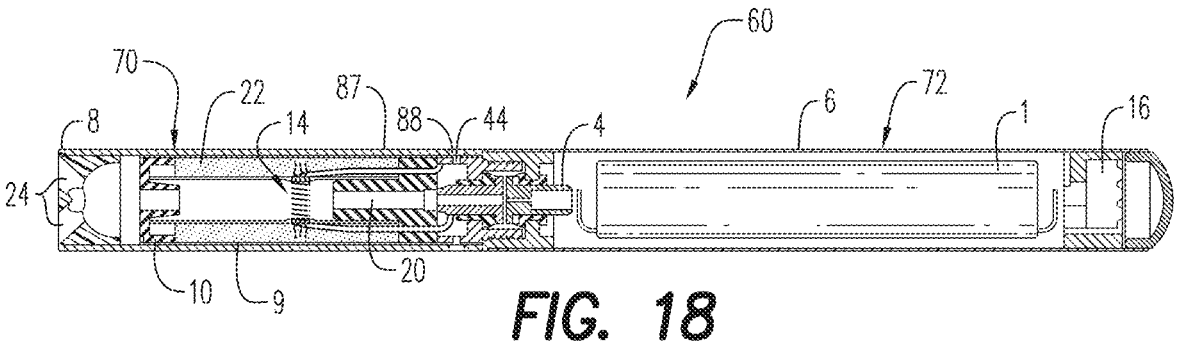
FIG. 18 is a cross-sectional view of an electronic cigarette according to the first embodiment and further including a sleeve assembly.

As shown in FIG. 18, the electronic cigarette 60 can also include a sleeve assembly 87 removably and/or rotatably positioned about a first section 70 of the electronic cigarette 70. Moreover, the sleeve assembly 87 insulates at least a portion of the first section 70 so as to maintain the temperature of the aerosol prior to delivery to the smoker. In the preferred embodiment, the sleeve assembly 87 is rotatable about the electronic cigarette 60 and includes spaced apart slots 88 arranged transversely about the sleeve assembly such that the slots 88 line up with the air inlets 44, 44' in the first section 70 to allow air to pass into the electronic cigarette 60 when a smoker draws a puff. Before or during smoking, the smoker can rotate the sleeve assembly 87 such that the air inlets 44, 44' are at least partially blocked by the sleeve assembly 87 so as to adjust the resistance to draw and/or ventilation of the electronic cigarette 60 if desired.

Preferably, the sleeve assembly 87 is made of silicone or other pliable material so as to provide a soft mouthfeel to the smoker. However, the sleeve assembly 87 can be formed in one or more pieces and can be formed of a variety of materials including plastics, metals and combinations thereof. In a preferred embodiment, the sleeve assembly 87 is a single piece formed of silicone. The sleeve assembly 87 can be removed and reused with other electronic cigarettes or can be discarded along with the first section 70. The sleeve assembly 87 can be any suitable color and/or can include graphics or other indicia.

Aroma Delivery

As shown in FIG. 11, the electronic cigarette 60 can also include an aroma strip 89 located on an outer surface 91 of at least one of the first section 70 and the second section 72. Alternatively, the aroma strip 89 can be located on a portion of the sleeve assembly 87. Preferably, the aroma strip 89 is located between the battery of the device and the heater 14 such that the aroma strip 89 is adjacent a smoker's nose during smoking. The aroma strip 89 can include a flavor aroma gel, film or solution including a fragrance material that is released before and/or during smoking.

In one embodiment, the flavor aroma of the gel, fluid and/or solution can be released by the action of a puff which may open a vent over the aroma strip when positioned inside the first section 70 (not shown). Alternatively, heat generated by the heater 14 can cause the release of the aroma.

In one embodiment, the aroma strip 89 can include tobacco flavor extracts. Such an extract can be obtained by grinding tobacco material to small pieces and extracting with an organic solvent for a few hours by shaking the mixture. The extract can then be filtered, dried (for example with sodium sulfate) and concentrated at controlled temperature and pressure. Alternatively, the extracts can be obtained using techniques known in the field of flavor chemistry, such as the Solvent Assisted Flavor Extraction (SAFE) distillation technique (Engel et al. 1999), which allows separation of the volatile fraction from the non-volatile fraction. Additionally, pH fractionation and chromatographic methods can be used for further separation and/or isolation of specific compounds. The intensity of the extract can be adjusted by diluting with an organic solvent or water.

The aroma strip 89 can be a polymeric or paper strip to which the extract can be applied, for example, using a paintbrush or by impregnation. Alternatively, the extract can be encapsulated in a paper ring and/or strip and released manually by the smoker, for example by squeezing during smoking the aroma strip.

In one embodiment, the electronic cigarette 60 of FIGS. 2, 5, 7 and 9 can also include a filter segment upstream of the heater 14 and operable to restrict flow of air through the electronic cigarette 60. The addition of a filter segment can also aid in adjusting the resistance to draw.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions.

It will now be apparent that a new, improved, and non-obvious electronic cigarette has been described in this specification with sufficient particularity as to be understood by one of ordinary skill in the art. Moreover, it will be apparent to those skilled in the art that numerous modifications, variations, substitutions, and equivalents exist for features of the electronic cigarette which do not materially depart from the spirit and scope of the invention. Accordingly, it is expressly intended that all such modifications, variations, substitutions, and equivalents which fall within the spirit and scope of the invention as defined by the appended claims shall be embraced by the appended claims.

We claim:

1. A cartridge comprising:
an outer housing extending in a longitudinal direction, the outer housing defining at least one air inlet in the outer housing;
a heater in the outer housing;
a mouthpiece at a mouth-end of the outer housing;
a sleeve assembly extending about an exterior of the outer housing and over at least a portion of the mouth-end, the sleeve assembly configured to rotate about the outer housing, the sleeve assembly defining spaced apart slots configured to align with the at least one air inlet such that ventilation may be adjusted, and the sleeve assembly formed of silicone so as to provide a soft mouthfeel; and
a connector piece at an end of the cartridge opposition the mouth-end, the at least one air inlet between the connector piece and the mouthpiece.

2. The cartridge of claim 1, further comprising:
a reservoir in the outer housing, the reservoir configured to store a pre-vapor formulation.

3. The cartridge of claim 2, further comprising:
a wick in communication with the reservoir.

4. The cartridge of claim 3, wherein the wick includes a plurality of filaments.

5. The cartridge of claim 3, wherein the heater extends along a length of the wick.

6. The cartridge of claim 2, further comprising:
an inner tube in the outer housing, at least a portion of the reservoir between the outer housing and the inner tube.

7. The cartridge of claim 6, wherein
the inner tube includes a pair of opposing slots, and
end portions of the heater extend through the opposing slots.

8. The cartridge of claim 6, wherein the inner tube is formed of a woven fiberglass material.

9. The cartridge of claim 6, wherein the inner tube has a diameter of 4 mm.

10. The cartridge of claim 1, wherein the heater is a coil heater.

11. The cartridge of claim 10, wherein the coil heater is formed of a nickel-chromium alloy.

12. The cartridge of claim 11, wherein the nickel-chromium alloy is iron-free.

13. The cartridge of claim 10, wherein the coil heater comprises 3 to 8 windings.

14. The cartridge of claim 1, wherein the heater is unbowed along a length thereof.

15. The cartridge of claim 1, further comprising:
an aroma strip on an outer surface of the outer housing, the aroma strip located between a battery and the heater.

16. The cartridge of claim 1, further comprising:
a filter segment between the heater and the mouthpiece.

17. An electronic vaping device comprising:
a cartridge including,
a first outer housing extending in a longitudinal direction, the first outer housing defining at least one air inlet in the first outer housing of the cartridge,
a heater in the first outer housing,
a mouthpiece at a mouth-end of the first outer housing, and
a sleeve assembly extending about an exterior of the first outer housing and over at least a portion of the mouth-end, the sleeve assembly configured to rotate about the first outer housing, the sleeve assembly defining spaced apart slots configured to align with the at least one air inlet such that ventilation may be adjusted, and the sleeve assembly formed of silicone so as to provide a soft mouthfeel;
a battery section including,
a second outer housing, and
a power supply configured to supply power to the heater; and
a connection configured to connect the cartridge and the battery section.

18. The electronic vaping device of claim 17, wherein
the heater is a coil heater,
the coil heater is formed of a nickel-chromium alloy,
the nickel-chromium alloy is iron-free, and
the coil heater comprises 3 to 8 windings.

* * * * *